US009593931B2

United States Patent
Tench et al.

(10) Patent No.: US 9,593,931 B2
(45) Date of Patent: Mar. 14, 2017

(54) PALLADIUM COATING THICKNESS MEASUREMENT

(71) Applicant: ECI Technology, Inc., Camarillo, CA (US)

(72) Inventors: D. Morgan Tench, Camarillo, CA (US); Michael Pavlov, Fair Lawn, NJ (US); Eugene Shalyt, Washington Township, NJ (US); Peter Bratin, Flushing, NY (US); Vladimir Dozortsev, Ridgewood, NJ (US)

(73) Assignee: ECI Technology, Inc., Totowa, NJ (US)

( * ) Notice: Subject to any disclaimer, the term of this patent is extended or adjusted under 35 U.S.C. 154(b) by 681 days.

(21) Appl. No.: 14/016,120

(22) Filed: Sep. 1, 2013

(65) Prior Publication Data

US 2014/0061064 A1    Mar. 6, 2014

Related U.S. Application Data

(60) Provisional application No. 61/743,627, filed on Sep. 4, 2012.

(51) Int. Cl.
*G01B 7/00* (2006.01)
*G01B 7/06* (2006.01)
*G01N 27/26* (2006.01)

(52) U.S. Cl.
CPC ............ *G01B 7/085* (2013.01); *G01N 27/26* (2013.01)

(58) Field of Classification Search
CPC ....... G01N 27/4161; G01B 7/06; G01B 7/085
See application file for complete search history.

(56) References Cited

U.S. PATENT DOCUMENTS 5,262,022 A * 11/1993 Tench .................... B23K 1/206
                                                            204/400

OTHER PUBLICATIONS

P. Bratin, et al. "Study of Precious Metal Coatings Using Sequential Electrochemical Reduction Analysis" Metal Finishing, Oct. 1996, p. 10, 12, 14-15.*
M. Pavlov, et al. "Electrochemical approach and apparatus for analysis of oxides located on the surface of copper wires" Abstract #2013, 218th Electrochemical Society Meeting, 2010.*

* cited by examiner

*Primary Examiner* — J. Christopher Ball
(74) *Attorney, Agent, or Firm* — D. Morgan Tench

(57) ABSTRACT

The thickness of a palladium coating on copper (or another substrate) is measured by passing a cathodic current through a predetermined area of the coating in contact with an electrolytic solution and measuring the potential as a function of time. Protons from the electrolytic solution are electrochemically reduced to palladium hydride at cathodic potentials less negative than required for evolution of hydrogen. As formation of the $PdH_{0.58}$ beta-phase throughout the Pd coating is completed, the cathodic potential increases rapidly to a cathodic potential plateau corresponding to evolution of hydrogen gas on the $PdH_{0.58}$ surface. This step in the cathodic potential provides an endpoint time for the measurement. The absolute thickness of the Pd coating is calculated from the integrated cathodic charge passed up to the endpoint time and the predetermined area of the coating in contact with the electrolytic solution.

27 Claims, 13 Drawing Sheets

PALLADIUM COATING THICKNESS MEASUREMENT

CROSS-REFERENCE TO RELATED APPLICATIONS

This application claims priority to U.S. Provisional Patent Application No. 61/743,627 to Tench et al. filed 4 Sep. 2012, which is assigned to the same assignee.

BACKGROUND OF THE INVENTION

Field of the Invention

This invention is concerned with control of microelectronic assembly processes, and in particular with measuring the thickness of palladium layers in surface finishes.

Description of the Related Art

Surface finishes comprising a palladium outer layer are widely used by the electronics industry to protect copper substrates from oxidation so as to ensure solderability and wire bondability of bonding wire, device leads, leadframes, printed wiring boards and surface pads. A nickel underlayer is often used to prevent cracking of the palladium coating and exposure of the copper substrate. It is necessary to control the thickness of the palladium layer so as to provide adequate oxidation resistance to the substrate with a minimum amount of palladium, which is a relatively expensive metal.

Palladium thickness is typically measured in the prior art by x-ray fluorescence (XRF), which requires relatively complicated and expensive instrumentation and is difficult to apply to the odd geometries and small specimen areas typical of microelectronic devices. A recent study by S. Dill and V. Rössiger [Circuit World 37(2), 220-226 (2011)] found that the well-established XRF instrumentation with proportional counter detectors is not very suitable for measuring the thickness of thin palladium coatings (<0.1 µm) due to poor energy resolution of the proportional counter-tubes. These workers also found that semiconductor detector systems provide more reliable XRF thickness measurements with significantly higher accuracy but require special x-ray optics (polycapillaries) for small measuring spots (e.g. 0.15 µm). In any case, the effect of the composition of the substrate base material must be taken into account by the XRF software evaluation algorithm for each measurement. A global base material subtraction performed prior to the measurement can provide better repeatability but can also lead to incorrect absolute values of the thickness [S. Dill and V. Rössiger, Circuit World 37(2), 220-226 (2011)].

SUMMARY OF THE INVENTION

The invention provides a method and an apparatus for measuring a thickness of a palladium (Pd) coating on a substrate by determining the electrical charge required to form a palladium hydride having a specific stoichiometry, preferably $PdH_{0.58}$ (beta-phase), throughout the coating thickness by electrochemical reduction of protons from an electrolytic solution. A predetermined area of the Pd coating in contact with the electrolytic solution serves as a working electrode in an electrochemical cell, which also comprises a counter electrode and preferably a separate reference electrode that are also in contact with the electrolytic solution. The predetermined area of the coating (working electrode) is preferably defined by a gasket or an o-ring but may be defined by any suitable means, including an adhesive maskant, a curable resin maskant, a gelled electrolytic solution, partial or total immersion of the Pd coating in the electrolytic solution, or combinations thereof. Preferably, the electrolytic solution is a buffer solution of high buffering capacity and, when necessary, is deaerated to avoid interference from oxygen reduction at the working electrode.

The method of the invention comprises a cathodic embodiment and an anodic embodiment. According to the cathodic embodiment, the Pd thickness is determined from the cathodic charge density required to cathodically form a palladium hydride throughout the Pd coating by reduction of protons at the surface of the coating in contact with an electrolytic solution. According to the anodic embodiment, a cathodic pretreatment is used to saturate the palladium coating with palladium hydride and the coating thickness is determined from the anodic charge density required to anodically remove the palladium hydride by electrochemical oxidation. For a specific palladium thickness, the cathodic charge density required to form the palladium hydride throughout the Pd coating thickness is equivalent in absolute magnitude to the anodic charge density required to remove the palladium hydride throughout the Pd coating thickness.

In a preferred cathodic embodiment, the electrochemical proton reduction is performed chronopotentiometrically by applying a cathodic current to the working electrode and measuring the potential of the working electrode (preferably relative to a separate reference electrode) as a function of time. As formation of the $PdH_{0.58}$ beta-phase throughout the Pd coating approaches completion, the cathodic potential of the working electrode increases rapidly to a cathodic plateau corresponding to evolution of hydrogen gas on the $PdH_{0.58}$ surface. The resulting cathodic potential step in a plot of the working electrode potential as a function of time provides a cathodic endpoint time that can be used to calculate the thickness of the Pd coating. The applied cathodic current may be held constant or be varied with time. For a constant applied current, the current multiplied by the time interval from application of the cathodic current to the cathodic endpoint time yields the charge required to form the $PdH_{0.58}$ beta-phase throughout the Pd coating. In this case, the thickness of the Pd coating can be calculated according to the equation:

$$\text{Pd thickness in } \mu m = \frac{(\text{current density in mA/cm}^2)(\text{time interval in seconds})}{632 \text{ mC/cm}^2 - \mu m}.$$

Since the method provides an absolute measure of the coating thickness (no adjustable parameters), it is aptly termed the PATA (Palladium Absolute Thickness Assessment) method. If the coating thickness varies within the predetermined area of the coating used for the measurement, the method provides an average coating thickness.

In another cathodic embodiment of the method of the invention, the electrochemical proton reduction is performed chronoamperometrically by applying a cathodic potential to the working electrode and measuring the resulting cathodic current as function of time. The applied cathodic potential may be held constant or be varied with time but the final potential should be sufficiently negative for formation of the $PdH_{0.58}$ beta-phase throughout the Pd coating but not so negative that hydrogen gas is evolved on the $PdH_{0.58}$ surface. For this embodiment, the measured cathodic current tends to decrease with time and then to plateau at a near-zero value as formation of the $PdH_{0.58}$ beta-phase throughout the Pd coating approaches completion. The onset of this zero current plateau provides the cathodic endpoint time needed to calculate the thickness of the Pd coating.

According to the anodic embodiment of the method of the invention, a cathodic current or potential is first applied to the working electrode (Pd coating) for a sufficient time to ensure formation of the $PdH_{0.58}$ beta-phase throughout the Pd coating. An anodic current or potential is then applied to electrochemically oxidize the palladium hydride back to Pd (in the working electrode) and protons (in the electrolytic solution) so as to chronopotentiometrically or chronoamperometrically determine the quantity of $PdH_{0.58}$ beta-phase present in the Pd coating. The anodic oxidation approach has the advantage that the electrolytic solution need not be deaerated since interference from oxygen reduction is not an issue for anodic processes.

The apparatus of the invention provides automated application of the method of the invention. A preferred apparatus of the invention comprises an electrochemical measurement system, a computing device having a memory element with a stored algorithm operative to effect at least the basic steps of a method of the invention, and a computer interface enabling the computing device to control the electrochemical analysis system so as to perform said basic steps of a method of the invention.

The electrochemical approach of the invention may be used to detect and/or remove palladium hydride initially present in a Pd coating. Such residual palladium hydride might be introduced during electrodeposition of a Pd coating and could significantly reduce the accuracy of the Pd thickness measurement. The quantity of residual hydrogen in a Pd coating may be determined directly by applying an anodic current or potential to the Pd coating and measuring the anodic charge required to oxidize the residual palladium hydride. The quantity of residual palladium hydride in a Pd coating may also be determined indirectly by applying a cathodic current or potential to the Pd coating and measuring the cathodic charge required to form the $PdH_{0.58}$ beta-phase throughout the Pd coating with and without an anodic pretreatment to remove the residual palladium hydride. Within the scope of the invention, an anodic pretreatment may be used to remove residual palladium hydride so as to improve the accuracy of the Pd thickness measurement.

DETAILED DESCRIPTION OF THE INVENTION

Figure 1:
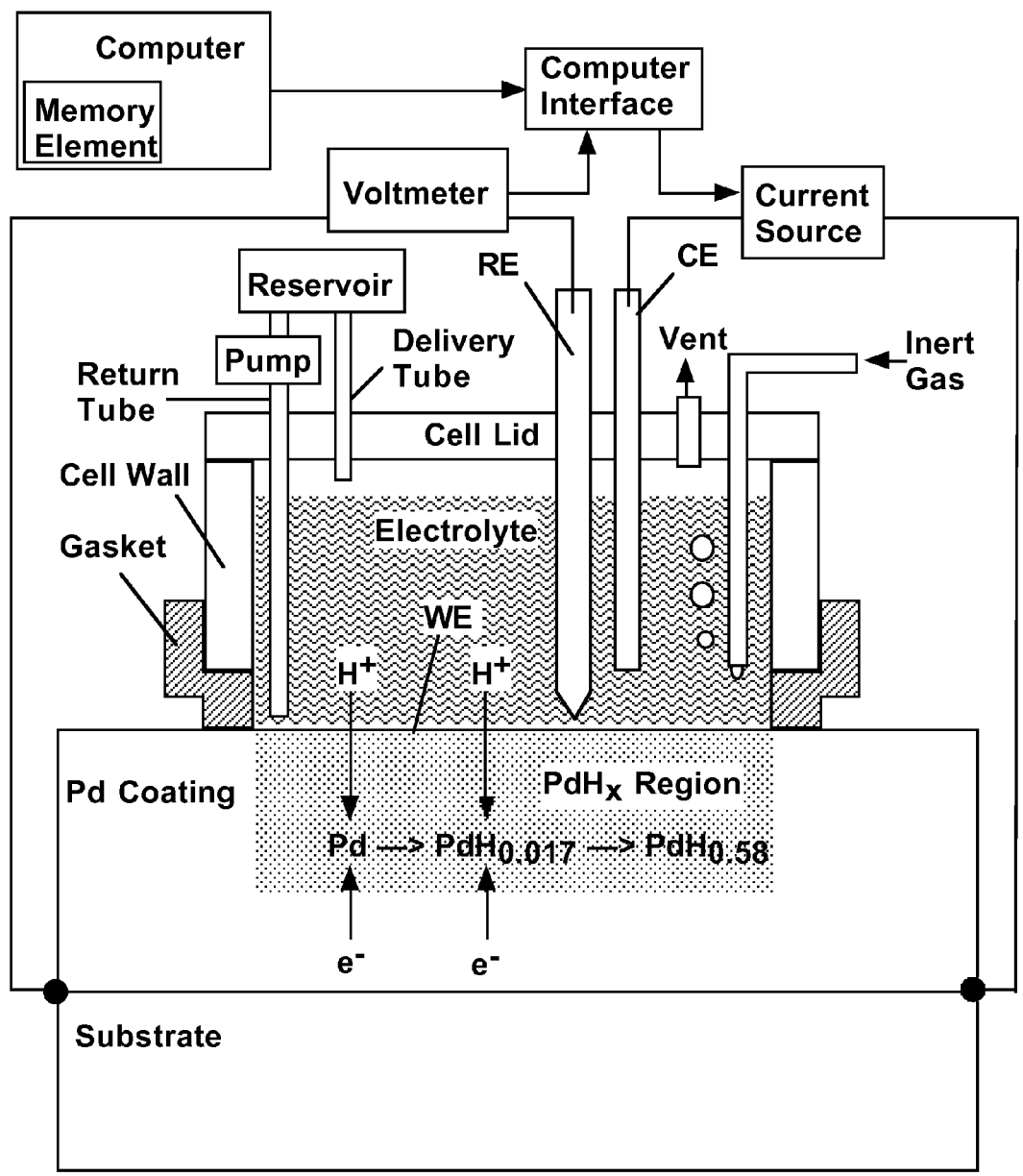
FIG. 1 schematically depicts a preferred embodiment of the apparatus of the invention, and illustrates proton reduction and palladium hydride formation according to the method of the invention.

Technical terms used in this document are generally known to those skilled in the art. The accepted convention is to use reduction potentials for electrochemical reactions for which more positive potentials tend to increase the rate of oxidation reactions and more negative potentials tend to increase the rate of reduction reactions.

A cathode is an electrode at which electrons flow from the electrode into an electrolytic solution so as to reduce species in the electrolytic solution. A cathodic potential is negative in the sense that an increase in a cathodic potential tends to increase the cathodic current for a reduction reaction. An applied cathodic current tends to drive the potential for a reduction reaction cathodic (in the negative direction).

An anode is an electrode at which electrons flow from an electrolytic solution into the electrode so as to oxidize species in the electrolytic solution. An anodic potential is positive in the sense that an increase in an anodic potential tends to increase the anodic current for an oxidation reaction. An applied anodic current tends to drive the potential for an oxidation reaction anodic (in the positive direction). Within the scope of the present invention, any applied current or potential may have a predetermined constant value or a predetermined waveform for which the current or potential is varied with time.

Electrode potentials reported in this document are reduction potentials versus a silver-silver chloride electrode (SSCE) reference. Data depicted graphically in curves or plots may be tabulated and used directly, especially by a computer, and the terms "curve" and "plot" include tabulated data.

A buffer solution is an electrolytic solution typically comprising a weak acid (acetic acid, for example) and a salt of the weak acid (sodium acetate, for example) for which the solution pH tends to remain at a constant value when protons are added to or removed from the solution. Buffering capacity is a measure of the capability of a buffer solution to maintain a constant pH value and generally increases as the concentrations of the buffer solution constituents are increased.

The invention provides a method and an apparatus for measuring the thickness of a Pd coating on a substrate by determining the electrical charge required to form (or remove) a palladium hydride throughout the coating thickness by electrochemical reduction (or oxidation) of protons (or palladium hydride) in an electrolytic solution. Since bulk palladium readily absorbs large quantities of hydrogen (via palladium hydride formation) whereas commonly-used substrate metals (copper and nickel, for example) absorb much less hydrogen, the invention can be applied to determine the thickness of Pd coatings on practically any substrate. Furthermore, since palladium forms a hydride (beta-phase) having a specific palladium/hydrogen ratio (1 to 0.58), the invention provides an absolute measure of the palladium thickness (without adjustable parameters). Consequently, the method of the invention is termed the PATA (Palladium Absolute Thickness Assessment) method.

The method of the invention for measuring a thickness of a palladium coating on a substrate, comprises the basic steps of: (1) placing a predetermined area of the palladium coating in contact with an electrolytic solution to form a working electrode; (2) placing a counter electrode and a reference electrode in contact with the electrolytic solution; (3) electrically connecting the working electrode and the counter electrode to an electrical power source, and the working electrode and the reference electrode to an electrical measuring device; (4) determining the charge density required to electrochemically form a palladium hydride throughout the thickness of the palladium coating; and (5) calculating the thickness of the palladium coating based on the charge density determined in Step (4). These steps may be performed in any reasonable order.

The method of the invention comprises a cathodic embodiment and an anodic embodiment. According to the cathodic embodiment, the Pd thickness is determined from the charge required to cathodically form a palladium hydride throughout the Pd coating thickness by reduction of protons at the surface of the coating in contact with an electrolytic solution. In this case, an anodization pretreatment may be used to remove any residual palladium hydride in the Pd coating prior to the cathodic analysis so as to improve the accuracy of the Pd thickness measurement. According to the anodic embodiment, the Pd thickness is determined from the charge required to anodically remove a palladium hydride (present throughout the Pd coating thickness) by electrochemical oxidation of the palladium hydride at the coating surface in contact with an electrolytic solution. In this case, a cathodic pretreatment is used to saturate the Pd coating with the palladium hydride prior to the anodic analysis.

A cathodic embodiment of the method of the invention for measuring the thickness of a palladium coating on a substrate comprises the steps of: (1) placing a predetermined area of the palladium coating in contact with an electrolytic solution to form a working electrode; (2) placing a counter electrode and a reference electrode in contact with the electrolytic solution; (3) electrically connecting the working electrode and the counter electrode to an electrical power source, and the working electrode and the reference electrode to an electrical measuring device; (4) applying at a cathodic start time a predetermined cathodic perturbation to the working electrode such that a cathodic current flows through the working electrode; (5) measuring an electrical response of the working electrode to the cathodic perturbation as a function of time; (6) determining a cathodic endpoint time corresponding to a relatively rapid change in the measured electrical response of the working electrode indicating formation of a palladium hydride throughout the thickness of the palladium coating; (7) integrating the cathodic current over the time interval between the cathodic start time and the cathodic endpoint time to provide a measured quantity of cathodic charge; and (8) calculating the thickness of the palladium coating based on the measured quantity of cathodic charge and the predetermined area of the Pd coating.

It would be apparent to those skilled in the art that a predetermined area of a coating for PATA testing may be defined by numerous means, depending on the geometry of the area to be tested. For a relatively flat test area, a gasket or an o-ring is preferred. A gasket or o-ring may also be used, in various configurations, for testing wire specimens. For example, a wire specimen may be passed through the openings in a pair of gaskets or o-rings that are compressed (via a fixture) so as to form two seals to the wire such that the length of wire therebetween defines the predetermined area. Alternatively, a wire specimen may be placed across an opening in a gasket or o-ring (or a pair of gaskets or o-rings) compressed (via a fixture) so as to seal off a section of the wire corresponding to the predetermined area. At least one groove may be included in at least one of the gaskets or o-rings to better accommodate the wire so as to form a better seal to the wire. For some specimen types, wires or component leads, for example, the predetermined area may be defined by simply immersing a test specimen or a portion thereof in the electrolytic solution. A maskant, an adhesive or a curable resin, for example, may be applied to define or better define the predetermined area. In some cases, the predetermined area may be defined via contact with a gelled electrolytic solution.

In a preferred cathodic embodiment, the electrical power source is a current source (a constant current power supply or a galvanostat, for example), the electrical measuring device is a voltmeter, the predetermined electrical perturbation is a predetermined cathodic current, the measured electrical response is the potential of the working electrode relative to the potential of the reference electrode, and the cathodic endpoint time corresponds to a cathodic step in the potential of the working electrode. In this case, a cathodic current of a predetermined magnitude or waveform is applied at the cathodic start time to the working electrode by means of the counter electrode and the current source, and the cathodic potential of the working electrode relative to the reference electrode potential is measured as a function of time. At the working electrode (Pd coating), protons are reduced to form palladium hydride, which is generally known to exist as an alpha-phase ($PdH_{0.017}$) for H/Pd atomic ratios of 0.017 or less and as a pure beta-phase ($PdH_{0.58}$) having a 0.58 H/Pd atomic ratio (under ambient conditions). The cathodic potential of the working electrode is initially positive of the hydrogen evolution potential (reflecting underpotential reduction of protons due to formation of palladium hydride) but increases rapidly until the alpha-phase approaches saturation, and thereafter more slowly until pure beta-phase is formed throughout the thickness of the Pd coating. As beta-phase formation is completed, the cathodic potential of the working electrode increases rapidly to a cathodic plateau potential corresponding to hydrogen evolution on the $PdH_{0.58}$ surface. This cathodic step in the potential of the working electrode provides a cathodic end-point time for the measurement. Integration of the cathodic current passed during the time interval between application of the cathodic current (cathodic start time) and the cathodic endpoint time yields the cathodic charge required to form $PdH_{0.58}$ throughout the thickness of the Pd coating, which is used to calculate the Pd coating thickness.

The cathodic current used for a PATA measurement may also be varied with time. For example, the magnitude of the applied cathodic current could be larger initially (to reduce the analysis time) and then be reduced to provide a sharper increase in the working electrode potential for more precise determination of the cathodic endpoint time. In this case, the measured cathodic charge needed to calculate the Pd coating thickness is provided by integrating the current over the time interval from the cathodic start time to the cathodic endpoint time.

In an alternative cathodic embodiment, the electrical power source is a voltage source, the electrical measuring device is an ammeter, the predetermined electrical perturbation is a predetermined working electrode potential, the measured electrical response is the cathodic current flowing through the working electrode, and the cathodic endpoint time corresponds to the onset of a substantially flat plateau in the cathodic current. In this cathodic embodiment, a cathodic potential of a predetermined magnitude or waveform is applied to the working electrode, and the cathodic current flowing through the working electrode is measured as a function of time. The voltage source is preferably a potentiostat which controls the potential of the working electrode relative to the potential of the reference electrode (by adjusting the current flowing between the working electrode and the counter electrode). The applied cathodic potential may be held constant or may be varied with time but the final potential should be sufficiently negative for formation of the $PdH_{0.58}$ beta-phase throughout the Pd coating but not so negative that hydrogen gas is evolved on the $PdH_{0.58}$ surface. In this case, the measured cathodic current tends to decrease as more palladium hydride is formed (underpotential for palladium hydride formation decreases), and then to plateau at a near-zero value as formation of the $PdH_{0.58}$ beta-phase throughout the Pd coating approaches completion. In this case, the onset of the cathodic plateau in a plot of the cathodic current as a function of time provides the cathodic endpoint time needed to calculate the thickness of the Pd coating. Integration of the cathodic current over the time interval from application of the cathodic potential (cathodic start time) to the cathodic endpoint time yields the cathodic charge required to form the $PdH_{0.58}$ beta-phase throughout the Pd coating, which is used to calculate the thickness of the Pd coating thickness.

In the anodic embodiment of the method of the invention, a cathodic current or potential is first applied to the working electrode for a sufficient time to ensure formation of the $PdH_{0.58}$ beta-phase throughout the Pd coating. An anodic current or potential is then applied to oxidize the palladium hydride back to Pd (in the working electrode) and protons (in the electrolytic solution) so as to chronopotentiometrically or chronoamperometrically determine the quantity of $PdH_{0.58}$ beta-phase present in the palladium hydride saturated coating. This anodic oxidation approach has the advantage that the electrolytic solution need not be deaerated since interference from oxygen reduction is not an issue for an anodic measurement. On the other hand, additional analysis time is required to form the palladium hydride throughout the Pd coating thickness prior to the anodic oxidation.

For the anodic chronopotentiometric embodiment, a predetermined anodic current is applied to a working electrode for which the Pd coating has been cathodically converted to $PdH_{0.58}$ beta-phase and the anodic potential of the working electrode is measured as a function of time. The anodic potential of the working electrode tends to increase slowly as the amount of palladium hydride in the working electrode decreases but increases sharply to an anodic plateau potential corresponding to oxygen evolution on the Pd surface when substantially all of the palladium hydride has been removed. The resulting anodic step in a plot of the working electrode potential as a function of time provides an anodic endpoint time that is used to calculate the thickness of the Pd coating.

For the anodic chronoamperometric embodiment, a predetermined anodic potential is applied to the working electrode for which the Pd coating has been cathodically converted to $PdH_{0.58}$ beta-phase and the anodic current flowing through the working electrode is measured as a function of time. For this embodiment, the applied anodic potential is chosen to be sufficiently positive for complete oxidation (removal) of the palladium hydride throughout the Pd coating thickness but not so positive that oxygen gas is evolved on the Pd surface. In this case, the measured anodic current decreases as more palladium hydride is removed by electrochemical oxidation (and the potential required for palladium hydride oxidation increases), and then plateaus at a near-zero value as removal of the palladium hydride throughout the Pd coating thickness approaches completion. The onset of the near-zero plateau in a plot of the anodic current as a function of time provides the anodic endpoint time needed to calculate the thickness of the Pd coating.

A preferred cathodic embodiment of the method of the invention for measuring a thickness of a palladium coating on a substrate comprises the steps of: (1) placing a predetermined area of the palladium coating in contact with an electrolytic solution to form a working electrode; (2) placing a counter electrode and a reference electrode in contact with the electrolytic solution; (3) electrically connecting the working electrode and the counter electrode to a current source, and the working electrode and the reference electrode to a voltmeter; (4) applying at a cathodic start time a predetermined cathodic current to the working electrode by means of the counter electrode and the current source such that a cathodic current flows through the working electrode; (5) measuring the potential of the working electrode as a function of time by means of the reference electrode and the voltmeter; (6) determining a cathodic endpoint time corresponding to a cathodic step in the measured potential of the working electrode indicating formation of a palladium hydride throughout the thickness of the palladium coating of the working electrode; (7) integrating the cathodic current over the time interval between the cathodic start time and the cathodic endpoint time to provide a quantity of cathodic charge passed; and (8) calculating the thickness of the palladium coating based on the quantity of cathodic charge passed and the predetermined area of the palladium coating. The predetermined cathodic current may be constant or varied with time.

An anodic embodiment of the method of the invention for measuring a thickness of a palladium coating on a substrate comprises the steps of: (1) placing a predetermined area of the palladium coating in contact with an electrolytic solution to form a working electrode; (2) placing a counter electrode and a reference electrode in contact with the electrolytic solution; (3) electrically connecting the working electrode and the counter electrode to an electrical power source, and the working electrode and the reference electrode to an electrical measuring device; (4) applying at a cathodic start time a predetermined cathodic perturbation to the working electrode such that a cathodic current flows through the working electrode; (5) measuring a cathodic response of the working electrode to the cathodic perturbation as a function of time at least until occurrence of a step in the measured cathodic response of the working electrode indicating formation of a palladium hydride throughout the thickness of the palladium coating of the working electrode; (6) applying at an anodization start time a predetermined anodic perturbation to the working electrode such that an anodic current flows through the working electrode; (7) measuring an anodic response of the working electrode to the anodic perturbation as a function of time; (8) determining an anodic endpoint time corresponding to a step in the measured anodic response of the working electrode indicating substantially complete removal of the palladium hydride within the predetermined working electrode area throughout the thickness of the palladium coating by electrochemical oxidation; (9) integrating said anodic current over the time interval between the anodization start time and the anodic endpoint time to provide an anodic charge required to electrochemically remove the palladium hydride throughout the thickness of the palladium coating within the predetermined area; and (10) dividing the anodic charge by the predetermined area of the palladium coating to calculate the anodic charge density required to electrochemically remove the palladium hydride throughout the thickness of the palladium coating, said anodic charge density being equivalent in absolute magnitude to the cathodic charge density required to form the palladium hydride throughout the thickness of the palladium coating. In this anodic embodiment, the predetermined cathodic perturbation may be a predetermined cathodic current or a predetermined cathodic potential of the working electrode, and the predetermined anodic perturbation may be a predetermined anodic current or a predetermined anodic potential of the working electrode. The predetermined anodic and cathodic potentials and currents may be constant or varied with time.

The counter electrode and the reference electrode of the invention may be the same electrode but are preferably separate electrodes. Preferably, the palladium hydride substantially comprises the $PdH_{0.58}$ beta-phase. A preferred electrolytic solution is an acetate buffer solution, preferably of pH 5.0 and comprising 2.0 M acetic acid and 2.0 M sodium acetate.

The counter electrode of the invention may comprise any suitable material. Preferably, the counter electrode comprises a metal that is stable against anodic oxidation, platinum or a stainless steel, for example, so that the electrolytic solution is not contaminated with anode oxidation products. If necessary, the counter electrode may be placed in a separate compartment separated from the electrochemical cell, via a porous frit, for example.

A wide variety of electrolytic solutions may be used to practice the invention. The primary function of the electrolytic solution is to supply protons for reduction at the Pd working electrode to produce palladium hydride, and in some embodiments to accept protons generated by oxidation of palladium hydride at the working electrode. An acidic electrolytic solution having a higher concentration of protons (lower pH) is preferred to avoid proton depletion at the higher current densities needed for short analysis times. On the other hand, strongly acidic electrolytic solutions may be difficult to handle and may render the Pd thickness measurement destructive by chemically attacking Pd coating underlayers and substrates. Proton depletion/accumulation in the electrolytic solution adjacent to the working electrode may be mitigated by flowing or stirring the solution so as to permit use of less acidic and/or less concentrated electrolytic solutions.

In a preferred embodiment, the electrolytic solution is a buffer solution, preferably having a pH in the 3.0 to 6.0 range, and most preferably in the 4.5 to 5.5 range. When practiced with a buffer solution in the preferred pH range, the method of the invention is typically nondestructive (depending on the application) so that a tested part need not be discarded. Examples of preferred buffer solutions (useful pH ranges in parentheses) include citric acid/sodium citrate (pH 3.0-6.2), acetic acid/sodium acetate (pH 3.7-5.6), and sodium hydroxide/potassium hydrogen phthalate (pH 4.1-5.9). The salt used to prepare the buffer solution may comprise various cations (sodium, potassium and/or ammonium, for example) and the concentrations of the constituents of the buffer solution may be varied over wide ranges (to adjust the pH and buffering capacity, for example).

A preferred buffer solution is an acetate buffer, which comprises acetic acid and an acetate salt (sodium acetate, potassium acetate, ammonium acetate or mixtures thereof, for example) at concentrations in the 0.1 to 10 M range. The buffer solution preferably has a high buffering capacity, which tends to increase with increased concentrations of the buffer constituents. When a nondestructive Pd thickness measurement is required, however, removal of acid and salt residues may be an issue for more concentrated buffer solutions. A most preferred buffer solution comprises 2.0 M acetic acid and 2.0 M sodium acetate (pH 5.0). Within the scope of the invention, electrolytic solutions having different compositions and/or constituent concentrations may be used for the anodic and cathodic portions of a PATA analysis.

In a simple embodiment of the invention, the counter electrode also serves as the reference electrode. In this case, errors in the measured working electrode potential may result from polarization of the counter electrode and ohmic potential losses due to current flow between the working and counter electrodes. Nonetheless, the counter electrode may also serve as the reference electrode in some cases, especially if the counter electrode has a relatively large surface area in contact with the electrolytic solution so that the current density at the counter electrode is small, and/or the counter electrode comprises a material that is not readily polarized in the electrolytic solution. Note that long-term stability of the reference electrode potential is not required for chronopotentiometric measurements according to the invention since the measurement endpoint time is indicated by a rapid change in the working electrode potential so that the actual potential value is not important. In this case, it is only necessary that the reference electrode potential remain substantially constant during each PATA measurement.

Use of a separate reference electrode is preferred to minimize the possibility of errors in the measured working electrode potential. Any suitable reference electrode may be used, for example, the silver-silver chloride electrode (SSCE) or the saturated calomel electrode (SCE), which are widely-used and commercially available.

Numerous voltmeters having high input impedance and accurate current sources suitable for practicing the invention are commercially available. For embodiments involving a potential applied to the working electrode, use of an electronic potentiostat and a separate reference electrode is preferred.

The invention further provides an apparatus for automated application of the method of the invention, which includes a computing device with a memory element having a stored algorithm operative to effect at least the basic steps of a method of the invention via an interface with suitable electronic and mechanical equipment. The apparatus of the invention for measuring the thickness of a palladium coating on a substrate comprises: (1) a measurement system, comprising (a) an electrolytic solution, (b) a means of placing a predetermined area of the palladium coating in contact with the electrolytic solution so as to form a working electrode, (c) a counter electrode and a reference electrode in contact with the electrolytic solution, (d) an electrical power source electrically connected to the working electrode and the counter electrode whereby a predetermined electrical perturbation is applied to the working electrode, (e) an electrical measuring device electrically connected to the working electrode and the reference electrode whereby an electrical response to the electrical perturbation applied to the working electrode is measured, and (f) a means of determining an endpoint time corresponding to a step in the electrical response of the working electrode; (2) a computing device having a memory element with a stored algorithm operative to effect at least the basic steps of a method of the invention comprising (a) determining the charge density required to electrochemically form a palladium hydride throughout the thickness of the palladium coating, and (b) calculating the thickness of the palladium coating based on the determined charge density; and (3) a computer interface enabling the computing device to control the electrochemical analysis system so as to perform said steps of the method of the invention. In a preferred embodiment, the stored algorithm of the computing device is operative to perform all of the steps of at least one of the anodic or cathodic embodiments of the method of the invention delineated above.

A preferred means of placing the predetermined area of the palladium coating in contact with the electrolytic solution so as to form a working electrode, comprises (a) a reservoir containing the electrolytic solution, (b) a delivery tube for conveying the electrolytic solution from the reservoir to the predetermined area of the palladium coating, (c) a return tube for conveying the electrolytic solution from the predetermined area of the palladium coating back to the reservoir or to a waste container, and (d) a liquid pump. Any suitable liquid pump may be used. Preferably, the stored algorithm of the computing device is also operative to place the predetermined area of the palladium coating in contact with the electrolytic solution to form the working electrode so as to provide fully automated operation.

FIG. 1 schematically depicts a preferred embodiment of the apparatus of the invention, and illustrates proton reduction and palladium hydride formation according to the method of the invention. For this preferred embodiment, a small gasket or o-ring is used to make a seal to the Pd coating so that the electrolytic solution can be placed in contact with a predetermined area of the Pd coating, which serves as a working electrode (WE). The gasket or o-ring may comprise any material that is chemically stable in the electrolytic solution and provides a good seal to the Pd coating surface. The electrolytic solution is preferably deaerated by passing an inert gas (nitrogen or argon, for example) through (or over) the electrolytic solution, preferably via a gas bubbler (as shown) or a gas dispersion tube. A counter electrode (CE) and a reference electrode (RE) in contact with the electrolytic solution are also depicted in FIG. 1.

To make a PATA measurement according to a preferred cathodic embodiment of the method of the invention with the preferred apparatus of FIG. 1, a predetermined cathodic current, which is preferably a constant current but may be varied with time, is applied at a cathodic start time to the Pd coating within the predetermined area (working electrode) by means of the current source and the counter electrode, while the potential of the working electrode (Pd coating) is measured relative to the potential of the reference electrode via a voltmeter. Protons electrochemically reduced at the working electrode (Pd coating) react with Pd to form a layer of palladium hydride, initially comprising $PdH_{0.017}$ (alpha-phase) that is converted to $PdH_{0.58}$ (beta-phase). When all of the Pd throughout the coating thickness within the working electrode area has been converted to $PdH_{0.58}$ (pure beta-phase), underpotential deposition of palladium hydride no longer occurs and the cathodic potential of the working electrode increases rapidly to the hydrogen evolution potential. This step in the working electrode potential provides a cathodic endpoint time for the measurement. The charge density (current density×time) required to convert all of the Pd throughout the coating thickness within in the working electrode area to $PdH_{0.58}$ provides an absolute measure of the Pd coating thickness.

Calculation of the Pd thickness is based on the assumptions that palladium hydride formation involves proton reduction in a one-electron electrochemical process and that the cathodic endpoint time corresponds to formation of the $PdH_{0.58}$ beta-phase throughout the Pd coating thickness. The equation for calculating the palladium thickness for a PATA measurement at constant current density was derived as follows:

$$\text{Pd weight/cm}^2 \text{ per } \mu m = (\text{Pd density}) \times (10^{-4} \text{ cm}/\mu m)$$
$$= 12.0 \text{ g/cm}^3 \times 10^{-4} \text{ cm}/\mu m$$
$$= 12.0 \times 10^{-4} \text{ g/cm}^2\text{-}\mu m$$

$$\text{Pd atoms/cm}^2 \text{ per } \mu m = \frac{(\text{grams Pd/cm}^2 \text{ per } \mu m)(\text{Avogadro's number})}{(\text{Pd atomic weight})}$$
$$= \frac{(12.0 \times 10^{-4} \text{ g/cm}^2\text{-}\mu m)(6.02 \times 10^{23} \text{ atoms/mole})}{(106.42 \text{ g/mole})}$$
$$= 6.8 \times 10^{18} \text{ Pd atoms/cm}^2\text{-}\mu m$$

$$\text{Charge/cm}^2 \text{ Per } \mu m \text{ Pd} = (6.8 \times 10^{18} \text{ Pd atoms/cm}^2\text{-}\mu m)(1.60 \times 10^{-19} \text{ C per electron})$$
$$= 1.09 \text{ C/cm}^2\text{-}\mu m$$
$$= 1090 \text{ mC/cm}^2\text{-}\mu m$$

$$\text{Charge/cm}^2 \text{ to } PdH_{0.58} = (\text{H/Pd atomic ratio of } PdH_{0.58})(\text{charge/cm}^2 \text{ per } \mu m \text{ Pd})$$
$$= 0.58 \times 1090 \text{ mC/cm}^2\text{-}\mu m$$
$$= 632 \text{ mC/cm}^2\text{-}\mu m$$

$$\text{Pd thickness in } \mu m = \frac{(\text{measured charge density in mC/cm}^2)}{632 \text{ mC/cm}^2\text{-}\mu m}$$
$$= \frac{(\text{current density in mA/cm}^2)(\text{time in seconds})}{632 \text{ mC/cm}^2\text{-}\mu m}$$

where the time corresponds to the interval between the cathodic start time and the cathodic endpoint time.

The preferred apparatus depicted in FIG. 1 further comprises a reservoir containing the electrolytic solution, delivery and return tubes running between the reservoir and the cell, and a liquid pump (preferably, an in-line liquid pump). To make a PATA measurement, a portion of the electrolytic solution in the reservoir is pumped to the electrochemical cell via the delivery tube. In this case, deaeration is preferably provided by continuously purging the electrolytic solution in the reservoir with an inert gas, the reference electrode is preferably placed in contact with the electrolytic solution in the reservoir, and the counter electrode is preferably placed in contact with the electrolytic solution in the return tube. During the PATA measurement, the electrolytic solution may be circulated via the delivery and return tubes so as to flow over the working electrode surface to minimize concentration polarization effects so that higher current densities may be used to reduce the analysis time. After the PATA measurement is completed, the portion of the electrolytic solution used for the measurement may be pumped back into the reservoir via the return tube.

The electrolytic solution in the reservoir should be replaced periodically to avoid buildup of contaminants (from electrochemical or chemical breakdown of buffer solution constituents and/or dissolution of substrate materials, for example) that may interfere with the Pd thickness analysis. Alternatively, the portion of the electrolytic solution used to make a PATA measurement may be discarded (pumped into a waste container, for example) to avoid contamination of the electrolytic solution in the reservoir.

The preferred apparatus of FIG. 1 further comprises a computer and a computer interface enabling the computer to control the electrochemical analysis system so as to automatically perform at least the basic steps of a method of the invention according to an algorithm stored in a memory element of the computer. The computer and the memory element may be integrated or separate devices. The memory element may be of any suitable type, including computer hard drive, microprocessor chip, read-only memory (ROM) chip, programmable read-only memory (PROM) chip, magnetic storage device, computer disk (CD) and digital video disk (DVD), for example.

Suitable power supplies, current sources, galvanostats, voltmeters, potentiostats, computing devices, memory elements and interfaces for use in the apparatus of the invention are well known to those skilled in the art. In a preferred embodiment, the measurement system, the computing device and the computer interface of the apparatus of the invention are substantially integrated in a single PATA measurement instrument. This instrument preferably comprises a separate reference electrode and a galvanostat for performing chronopotentiometric measurements, a potentiostat for performing chronoamperometric measurements, or both a galvanostat and a potentiostat.

Reduction to Practice

For reduction of the PATA method to practice, chronopotentiometric measurements were performed for two Pd/Cu standards (0.26 and 0.46 μm Pd thickness) in a stagnant acetate buffer solution under argon using a SurfaceScan® instrument (ECI Technology, Inc.). The Pd/Cu standards comprised a flat copper substrate with an electrodeposited Pd coating of a specified thickness (+/−5%).

To make a PATA measurement on such flat specimens with the SurfaceScan® instrument, deaerated buffer solution was pumped from a reservoir via a plastic delivery tube to a small circular area of the Pd coating defined by a gasket (0.32 cm diameter). For the present work, solution flow was stopped during the PATA measurements but solution circulation may be used to minimize concentration polarization due to proton depletion at the working electrode surface. After the PATA measurement was completed, the buffer solution was pumped via the return tube back to the reservoir. Alternatively, the portion of the electrolytic solution used to make a PATA measurement may be pumped into a waste container to avoid contamination of the electrolytic solution in the reservoir by species generated during the PATA measurements.

The buffer solution comprised 40 g of 28.5 wt. % NaOH and 24 g of glacial acetic acid in 1000 mL of solution for which the pH was adjusted by addition of more glacial acetic acid. The final solution comprised 0.29 M sodium acetate and 0.1M acetic acid and had a pH of 4.7 (measured with a pH meter). This buffer solution had a relatively low buffer capacity and was designated LC acetate buffer.

Figure 2:
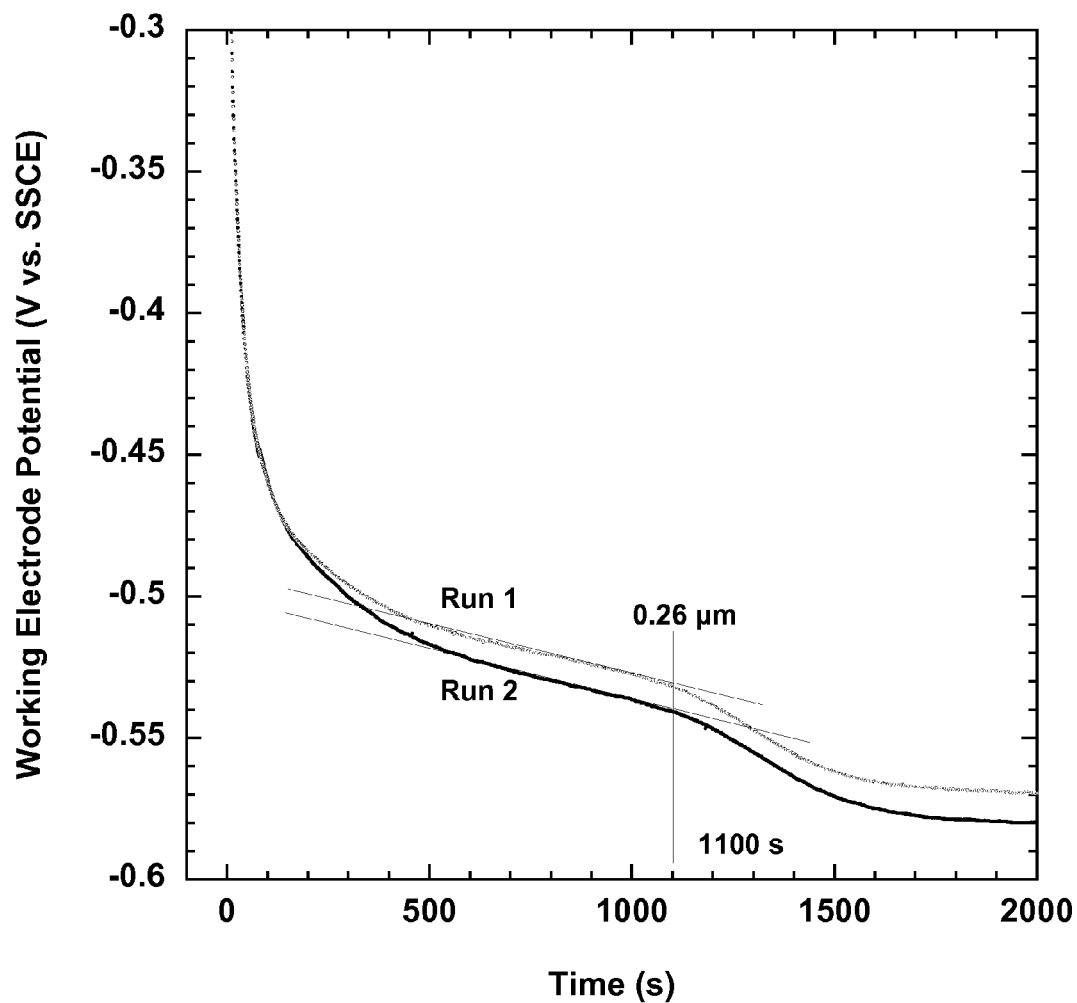
FIG. 2 shows PATA curves (two runs) for a first 0.26 μm Pd/Cu standard at −150 μA/cm$^2$ in the LC acetate buffer (pH 4.7).
Figure 3:
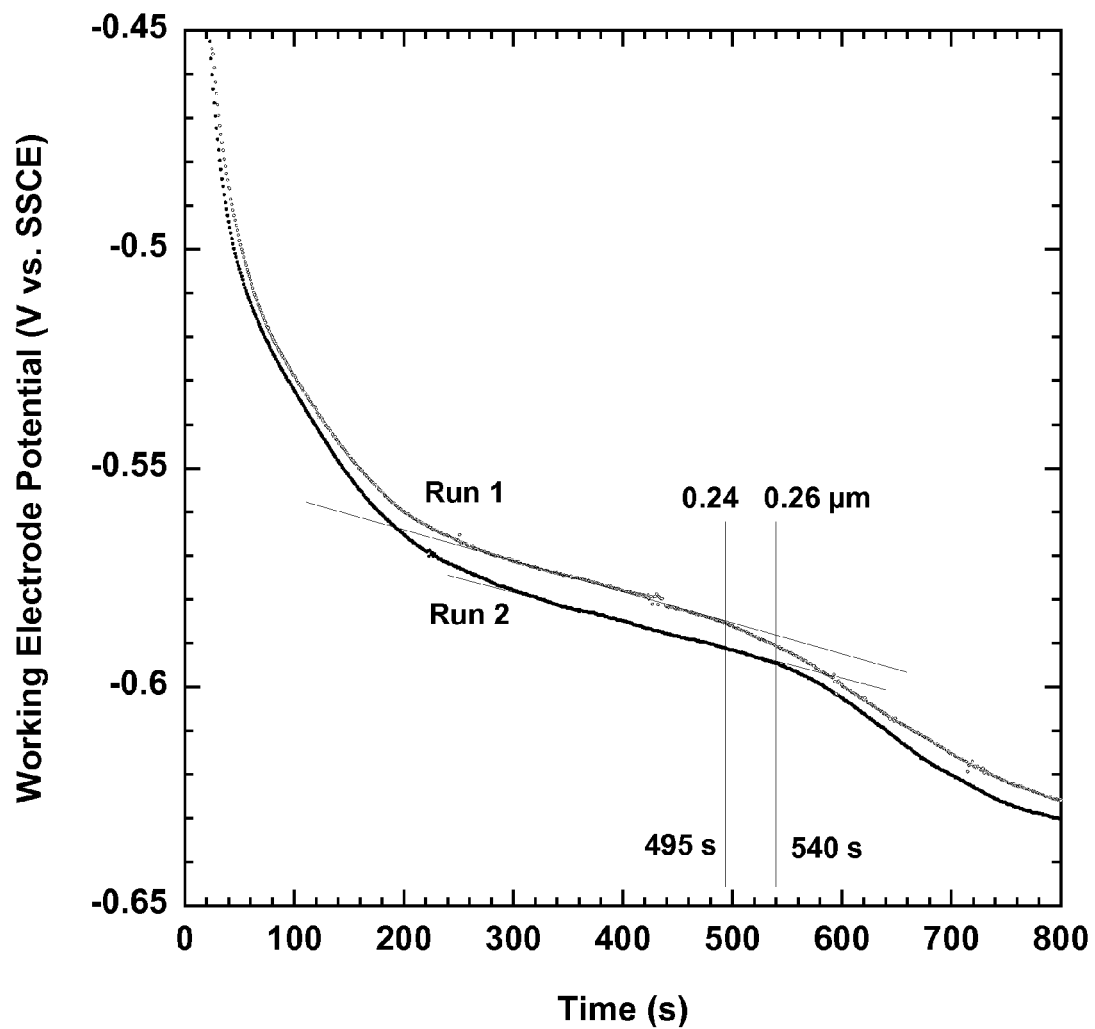
FIG. 3 shows PATA curves (two runs) for the first 0.26 μm Pd/Cu standard at −300 μA/cm$^2$ in the LC acetate buffer (pH 4.7).
Figure 4:
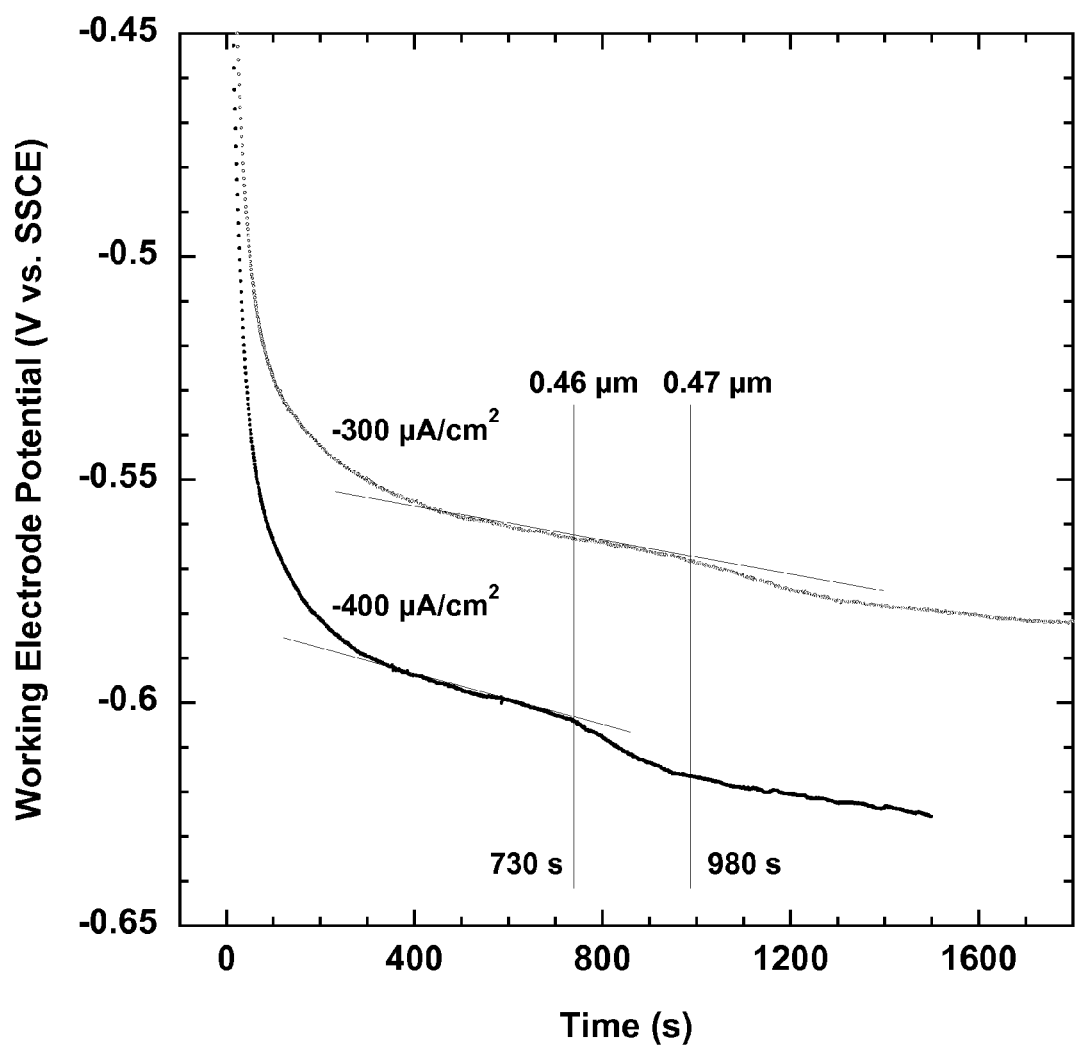
FIG. 4 shows PATA curves for a 0.46 μm Pd/Cu standard at two current densities (−300 and −400 μA/cm$^2$) in the LC acetate buffer (pH 4.7).

FIGS. 2, 3 and 4 show PATA curves (chronopotentiograms) obtained for duplicate runs at −150 μA/cm$^2$ (FIG. 2) and −300 μA/cm$^2$ (FIG. 3) for a first 0.26 μm standard, and single runs at −300 and −400 μA/cm$^2$ for a 0.46 μm standard (FIG. 4). The initial rapid increase in the cathodic potential of the working electrode is presumably associated with formation of the PdH$_{0.017}$ (alpha-phase) and the onset of the second rapid increase in the cathodic potential of the working electrode corresponds to substantially completed formation of the PdH$_{0.58}$ beta-phase throughout the coating thickness. As illustrated in the figures, the time corresponding to the onset of the second rapid increase in the cathodic potential of the working electrode was determined graphically and used to calculate the Pd layer thickness. Calculated values were 0.26, 0.26, 0.24 and 0.26 for the 0.26 μm standard, and 0.46 and 0.47 μm for the 0.46 μm standard. Agreement between the calculated and standard values was very good (within 0.02 μm).

Within the scope of the invention, any suitable feature of a PATA curve can be used to define and determine an endpoint time for a PATA analysis. Suitable features include an inflection point and an onset of a potential or current plateau or a negative step in working electrode potential or current. If necessary, an endpoint time correction may be applied to increase the accuracy of the Pd thickness determination.

Numerous graphical and mathematical methods suitable for determining an endpoint time of the invention from a PATA curve are available. The time corresponding to the onset of a rapid potential increase associated with formation of PdH$_{0.58}$ throughout the Pd coating thickness can readily be determined graphically. As discussed below with respect to a preferred embodiment, however, a differential method, which can be readily automated, is preferred.

Once formed, the palladium hydride layer is quite stable. If a PATA measurement is repeated on the same coating spot used for a previous PATA measurement, the cathodic potential of the working electrode increases rapidly to the hydrogen evolution potential and the cathodic potential plateau corresponding to palladium hydride formation is not observed. It is therefore important that the spots analyzed on a particular standard or analysis specimen do not overlap. It should be mentioned that the palladium hydride formation process can be reversed by reversing the polarity of the applied current (or by applying an anodic potential) so that the hydride in the coating is oxidized to protons in the electrolytic solution.

Although PATA measurements with the LC acetate buffer provided good accuracy and precision, the analysis time, especially for the thicker Pd coatings, was longer than desired (about 20 minutes for the 0.46 μm Pd/Cu coating at −400 μA/cm$^2$). At higher current densities with this and similar buffer solutions in the 4.0 to 5.0 pH range, sensitivity to the coating thickness tended to decrease, presumably because proton depletion at the working electrode surface became rate limiting. This issue could be addressed by increasing solution mass transport, by flowing the electrolytic solution over the working electrode surface, for example. Considerations in this case are increased complexity of the apparatus and electrical noise generated by a liquid pump. A better solution is to use a buffer solution of higher buffering capacity, which was found to be more important than the solution pH value.

Description of a Preferred Embodiment

In a preferred embodiment of the invention, the electrolytic solution is a buffer solution comprising 2.0 M sodium acetate+2.0 M acetic acid (pH 5.0). The very high buffering capacity of this VHC buffer solution provided consistent PATA results at high current densities (~1000 μA/cm$^2$) without solution flow. The higher current density also shortened the analysis time and provided a sharper endpoint.

Figure 5:
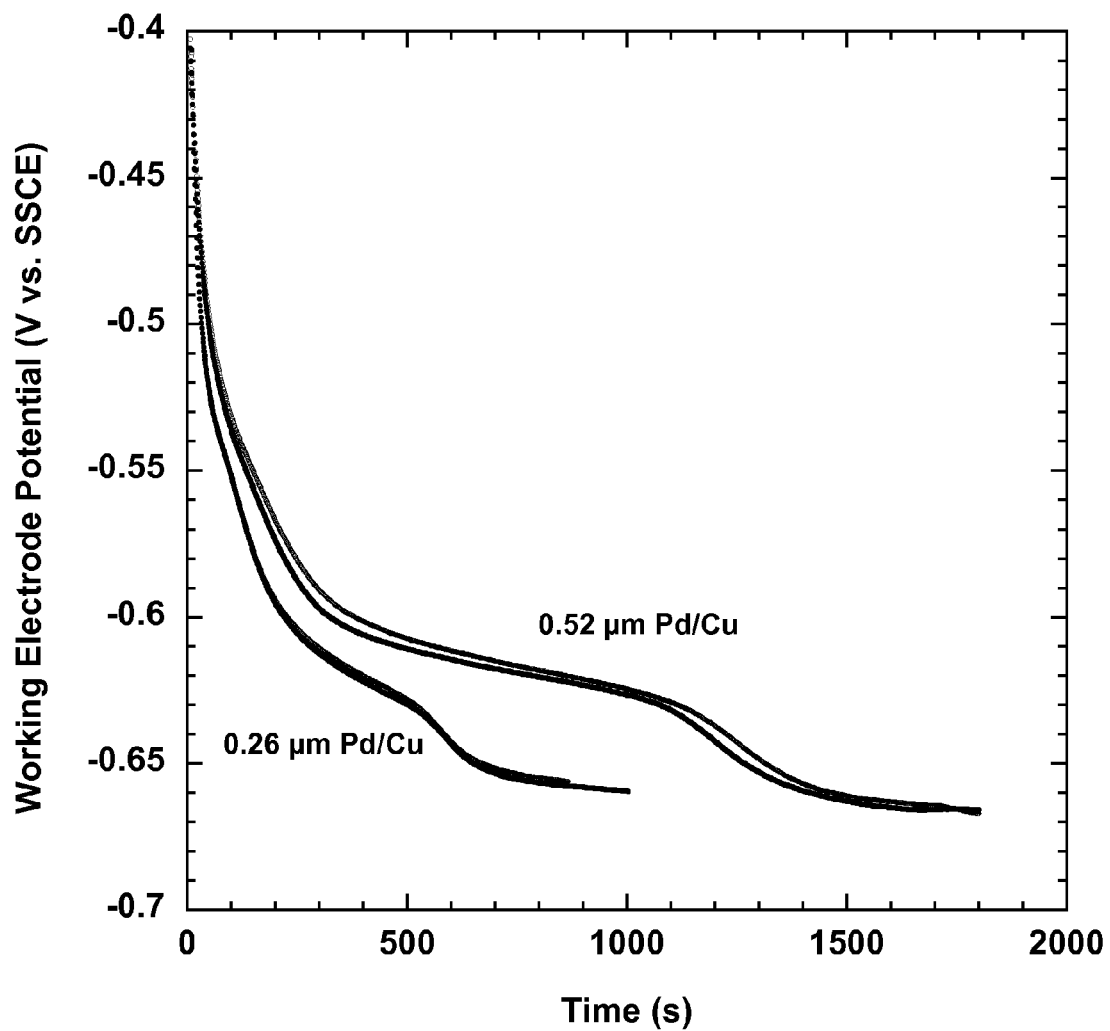
FIG. 5 shows PATA curves for duplicate runs at −300/tA/cm$^2$ for the first 0.26 μm standard and a first 0.52 μm Pd/Cu standard in the VHC acetate buffer (pH 5.0).

FIG. 5 shows PATA curves for duplicate runs at −300 μA/cm$^2$ for the first 0.26 μm Pd/Cu standard and a first 0.52 μm Pd/Cu standard in the VHC acetate buffer solution (pH 5.0). These curves are reproducible and very similar to those obtained for more dilute buffer solutions. The endpoint cathodic potential step is well-defined (approximately −40 mV) and the endpoint time correlates directly with the Pd thickness. The final cathodic potential plateau (corresponding to evolution of hydrogen gas) is practically flat.

Figure 6:
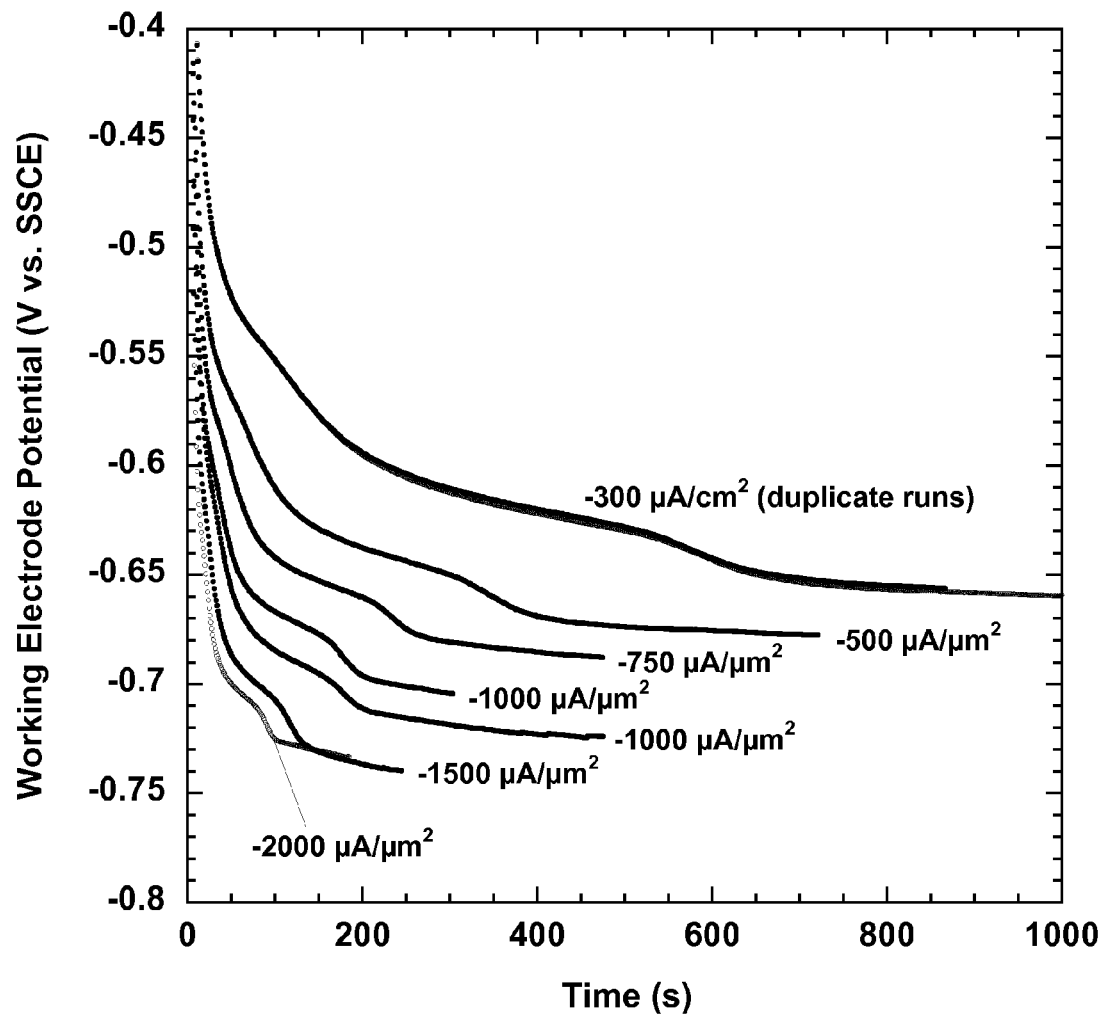
FIG. 6 shows PATA curves for the first 0.26 μm Pd/Cu standard at various current densities in the VHC acetate buffer (pH 5.0).

FIG. 6 shows PATA curves for the first 0.26 μm Pd/Cu standard at various cathodic current densities in the VHC acetate buffer solution (pH 5.0). The endpoint time remains well-defined but the curve at −2000 μA/cm$^2$ is apparently less dependent on the Pd thickness, indicating proton depletion at the electrode surface or that formation of PdH$_{0.58}$ has become rate limiting.

Figure 7:
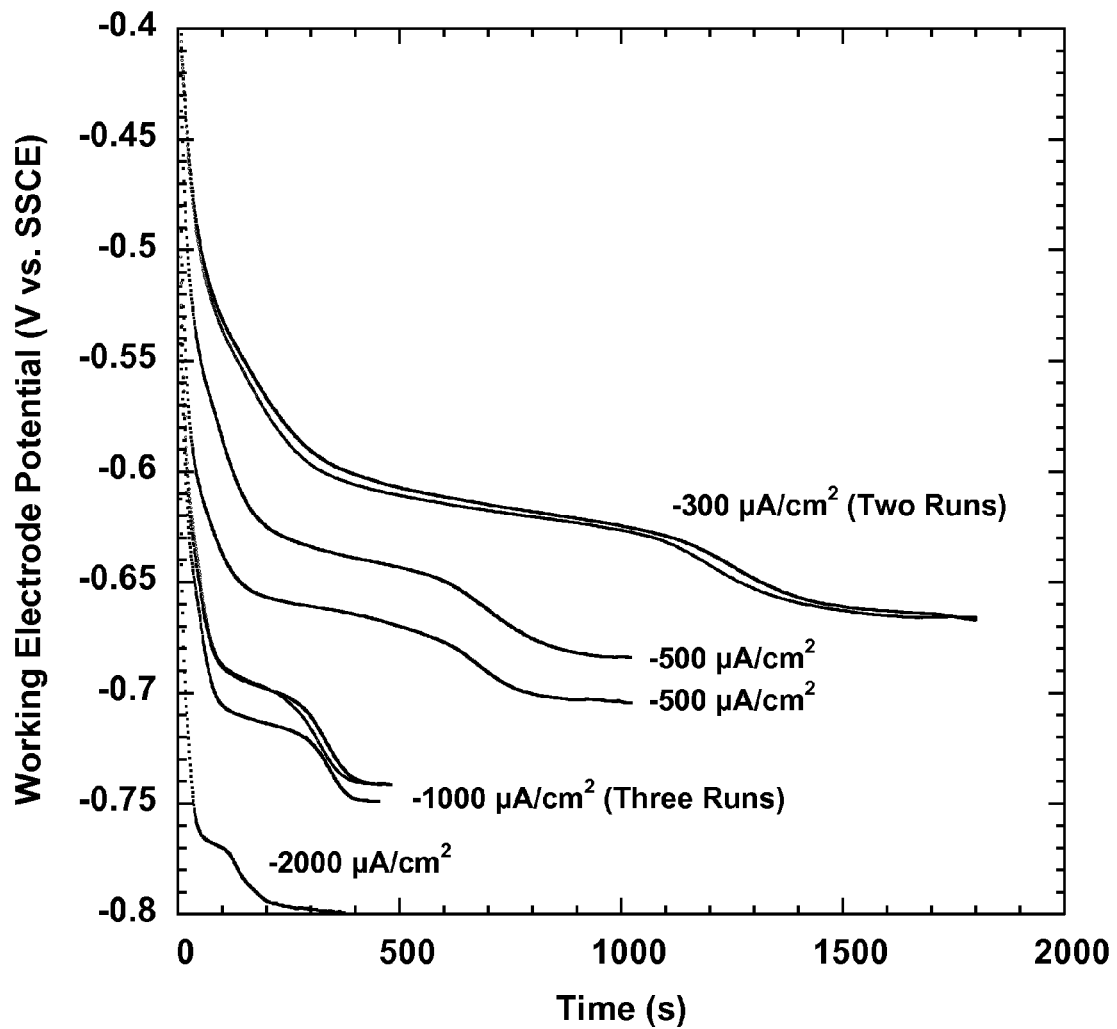
FIG. 7 shows PATA curves for the first 0.52 μm Pd/Cu standard at various current densities in the VHC acetate buffer (pH 5.0).

FIG. 7 shows PATA curves for the first 0.52 μm Pd/Cu standard at various cathodic current densities in the VHC acetate buffer (pH 5.0). The endpoint time remains well-defined and correlates with the current density. Note that the PATA curves for the two runs at −300 μA/cm$^2$ practically superimpose.

For detecting the endpoint time for a PATA measurement, a method that can readily be automated is preferred. Inspection of the PATA curves (FIGS. 2-10) reveals that the measured potential exhibits a first cathodic plateau during formation of the PdH$_{0.58}$ layer and a final cathodic plateau corresponding to hydrogen evolution, and the measured potential exhibits an inflection point between the two plateaux as the PdH$_{0.58}$ layer formation nears completion. Consequently, mathematical differentiation of the PATA curve should convert the inflection point to a negative peak (minimum) that can be used to quantitatively detect the endpoint time for the PATA measurement.

Figure 8:
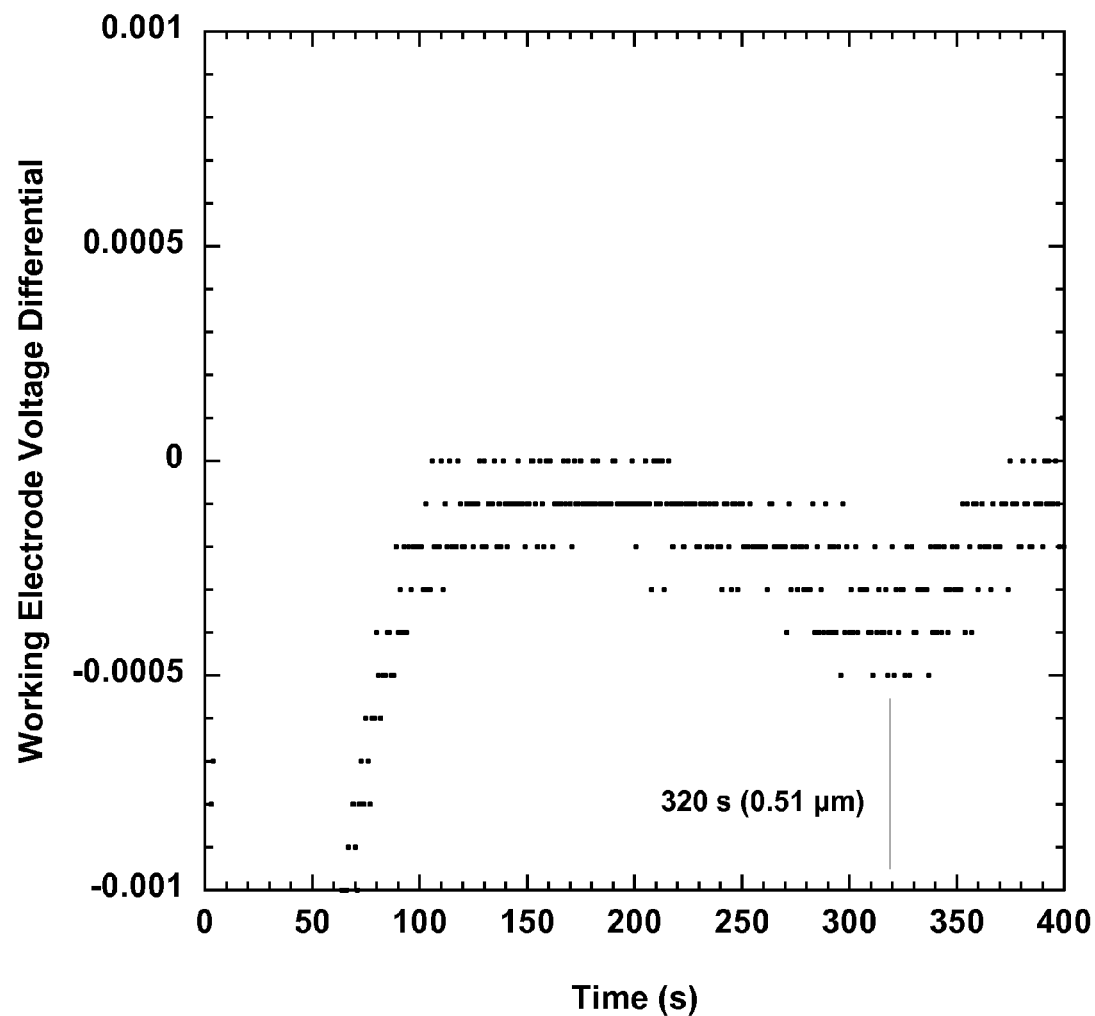
FIG. 8 shows a differential plot of a PATA curve for the first 0.52 μm Pd/Cu standard at −1000/μA/cm$^2$ in the VHC acetate buffer (pH 5.0).

FIG. 8 shows a differential plot of a PATA curve for the first 0.52 μm Pd/Cu standard at −1000/μA/cm$^2$ in the VHC acetate buffer (pH 5.0). This plot was constructed by simply taking the difference between the measured potentials for consecutive data points. Although the expected minimum is evident in the plot, the precision of the measured potentials was inadequate so that a banded plot with a broad minimum, rather than a smooth plot with a sharp minimum, was obtained. In this case, determination of the endpoint time is somewhat subjective and therefore uncertain. Nonetheless, simple differentiation of the PATA curve may provide acceptable results, depending on the precision of the potential measurements and the accuracy required for the endpoint time.

It is preferable, however, to mathematically smooth the PATA curve before differentiation to provide better resolution of the endpoint time. Within the scope of the invention, a PATA curve may be analyzed (to determine the endpoint time) by any suitable method, including those involving graphical analysis, mathematical differentiation, and mathematical smoothing and differentiation.

Figure 9:
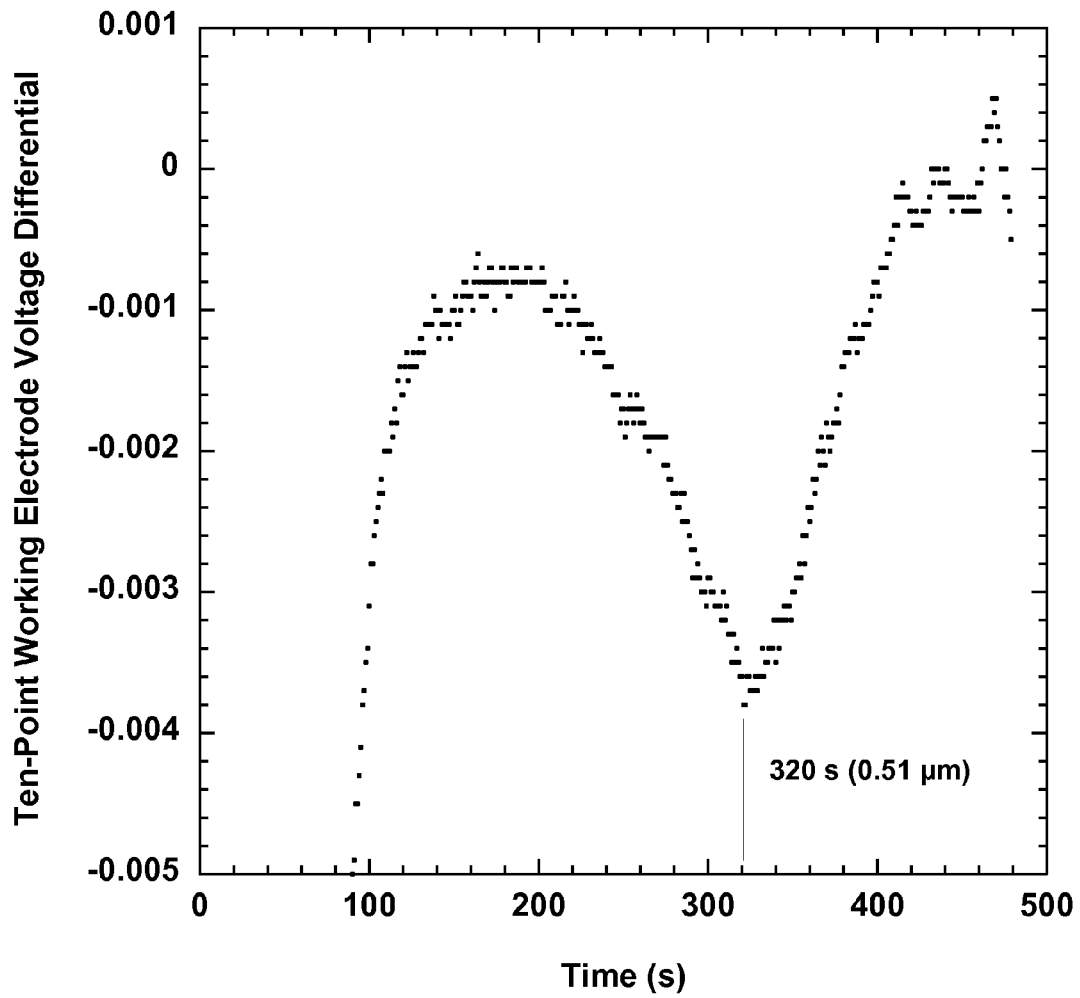
FIG. 9 shows a ten-point voltage differential plot of a PATA curve for the first 0.52 μm Pd/Cu standard at −1000 μA/cm$^2$ in the VHC acetate buffer (pH 5.0).

FIG. 9 shows a ten-point voltage differential plot of a PATA curve for the first 0.52 μm Pd/Cu standard at −1000 μA/cm$^2$ in the VHC acetate buffer (pH 5.0). For this plot, each point in the PATA curve (beginning with the 10$^{th}$ point) was replaced with a substitute point that was the sum of the potential for the point and the sum of the potentials for preceding nine points to provide a ten-point curve that retained the essential features of the PATA curve but consisted of data points of approximately ten-fold enhanced magnitude. The ten-point curve was then differentiated by taking the difference between consecutive enhanced data points. A well-defined minimum is evident in the ten-point voltage differential of FIG. 9, which yields a value of 0.51 μm for the Pd coating thickness.

Ten-point voltage differential plots were used to determine the endpoint times for the PATA curves (for the VHC acetate buffer) shown in FIGS. 5-9. The results are tabulated in Table 1. These data show that PATA measurements in a VHC acetate buffer provide a reliable measure of the absolute thickness of Pd coatings. Results at −2000 μA/cm$^2$ were less precise, apparently because of electrode polarization. A current density of −1000 μA/cm$^2$ provided a good compromise with respect to measurement precision and analysis speed. At this current density, the difference between the standard Pd thickness values (0.26 and 0.52 μm) and the measured values was never more than 0.03 μm.

TABLE 1

PATA Results for VHC Acetate Buffer Solution
with Ten-Point Voltage Differential Endpoint Determination

| Specimen | Pd (μm) | Current (μA/cm2) | Time (s) | Measured (μm of Pd) | Error (μm) | Error (%) |
|---|---|---|---|---|---|---|
| 0.26 μm (2nd) | 0.26 | 300 | 620 | 0.29 | 0.03 | 12 |
| 0.26 μm (2nd) | 0.26 | 300 | 535 | 0.25 | −0.01 | 4 |
| 0.26 μm (2nd) | 0.26 | 300 | 575 | 0.27 | 0.01 | 4 |
| 0.26 μm (1st) | 0.26 | 300 | 565 | 0.27 | 0.01 | 4 |
| 0.26 μm (1st) | 0.26 | 300 | 601 | 0.28 | 0.02 | 8 |
| 0.26 μm (1st) | 0.26 | 500 | 346 | 0.27 | 0.01 | 4 |
| 0.26 μm (2nd) | 0.26 | 500 | 356 | 0.28 | 0.02 | 8 |
| 0.26 μm (1st) | 0.26 | 750 | 240 | 0.28 | 0.02 | 8 |
| 0.26 μm (2nd) | 0.26 | 1000 | 171 | 0.27 | 0.01 | 4 |
| 0.26 μm (1st) | 0.26 | 1000 | 180 | 0.28 | 0.02 | 8 |
| 0.26 μm (1st) | 0.26 | 1000 | 185 | 0.29 | 0.03 | 12 |
| 0.26 μm (1st) | 0.26 | 1500 | 122 | 0.29 | 0.03 | 12 |
| 0.26 μm (1st) | 0.26 | 2000 | 95 | 0.3 | 0.04 | 15 |
| 0.52 μm | 0.52 | 300 | 1270 | 0.6 | 0.08 | 15 |
| 0.52 μm | 0.52 | 300 | 1223 | 0.58 | 0.06 | 12 |
| 0.52 μm | 0.52 | 300 | 1054 | 0.5 | −0.02 | 4 |
| 0.52 μm | 0.52 | 500 | 714 | 0.56 | 0.04 | 8 |
| 0.52 μm | 0.52 | 500 | 680 | 0.54 | 0.02 | 4 |
| 0.52 μm | 0.52 | 1000 | 345 | 0.54 | 0.02 | 4 |
| 0.52 μm | 0.52 | 1000 | 320 | 0.51 | −0.01 | 2 |
| 0.52 μm | 0.52 | 1000 | 329 | 0.52 | 0 | 0 |
| 0.52 μm | 0.52 | 2000 | 140 | 0.44 | −0.08 | 15 |

Within the scope of the invention, numerous mathematical approaches can be used to extract the endpoint time from a PATA curve. Depending on the approach used, there may be some deviation in the measured endpoint time. Errors in the Pd thickness determination introduced by such deviation are generally small. In any case, it is more important that the endpoint time be reproducible rather than correspond exactly to completed formation of a PdH$_{0.58}$ layer. If necessary, accuracy of the thickness measurement may be improved by analyzing a statistical number of standard specimens of precisely known Pd coating thickness to determine an endpoint calibration term to be added to or subtracted from the endpoint time or the calculated Pd thickness to correct for an endpoint deviation.

Figure 10:
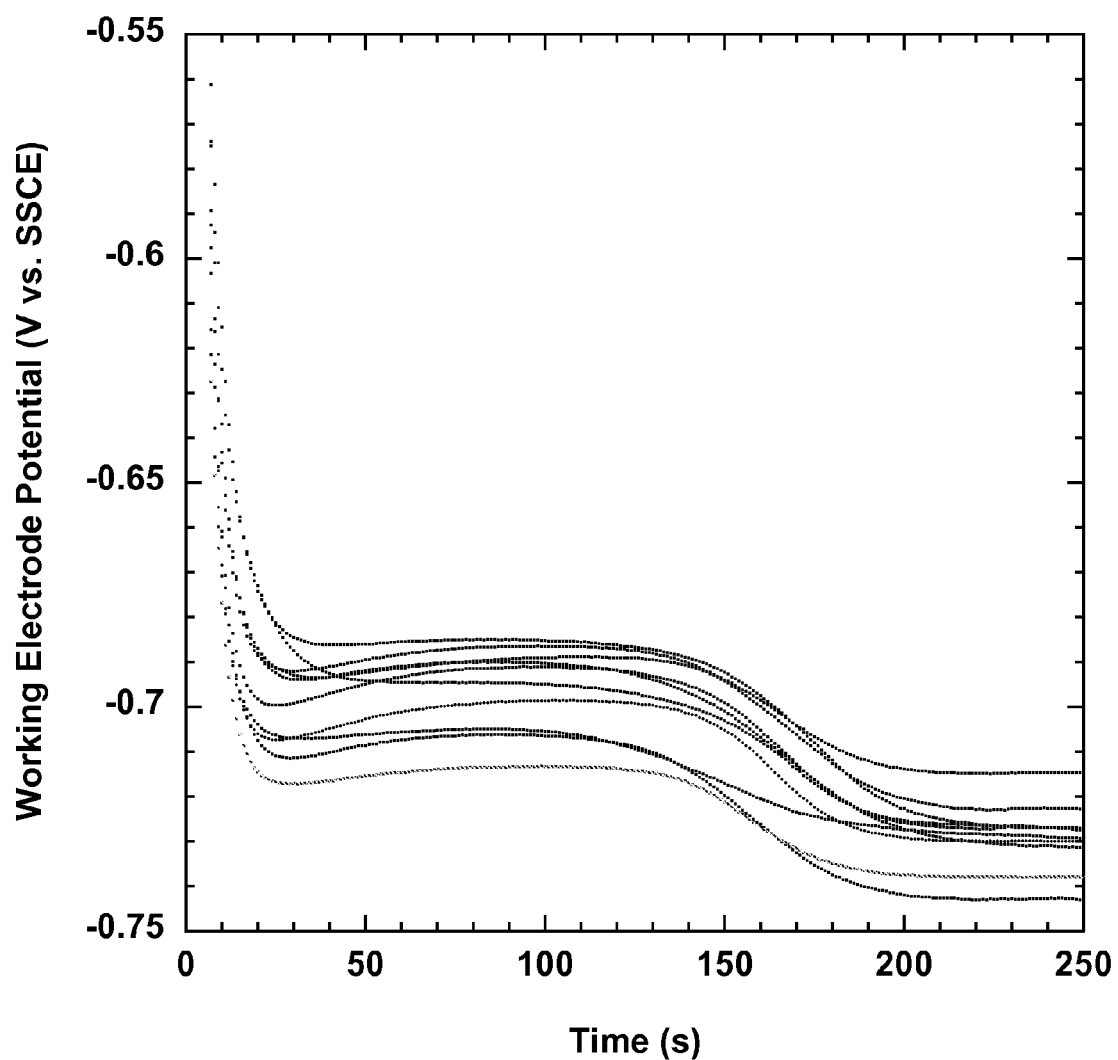
FIG. 10 shows ten repeated PATA curves for a third (new) 0.26 μm Pd/Cu standard at −1000 μA/cm$^2$ in the VHC acetate buffer solution (pH 5.0).
Figure 11:
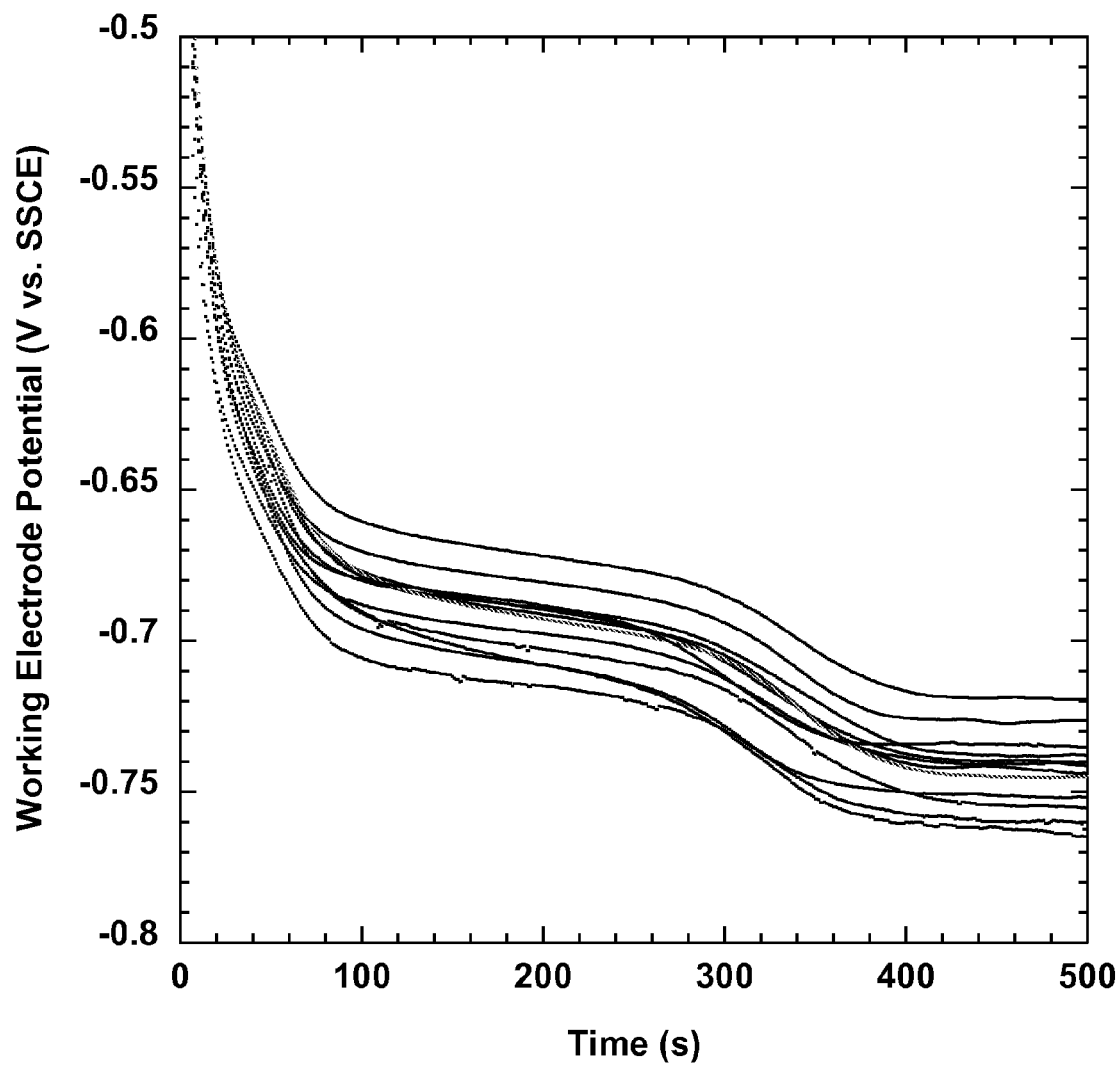
FIG. 11 shows twelve repeated PATA curves for a second (new) 0.52 μm Pd/Cu standard at −1000 μA/cm$^2$ in the VHC acetate buffer solution (pH 5.0).

The reproducibility and accuracy of the PATA method were evaluated in a nitrogen-saturated VHC acetate buffer solution at −1000/μA/cm$^2$ by repeating the PATA analysis ten times for a third (new) 0.26 µm Pd/Cu standard and twelve times for a second (new) 0.52 µm Pd/Cu standard. The PATA curves for the third 0.26 µm standard are shown in FIG. 10 and those for the second 0.52 µm standard are shown in FIG. 11. The cathodic potential plateaux for the PATA curves vary within a 30-mV range for the 0.26 µm standard, and within a 50-mV range for the 0.52 µm standard. These small potential shifts in the PATA curves may result from variations in the surface roughness of the Pd coatings on the Pd/Cu standards but in any case do not significantly affect the PATA results.

Figure 12:
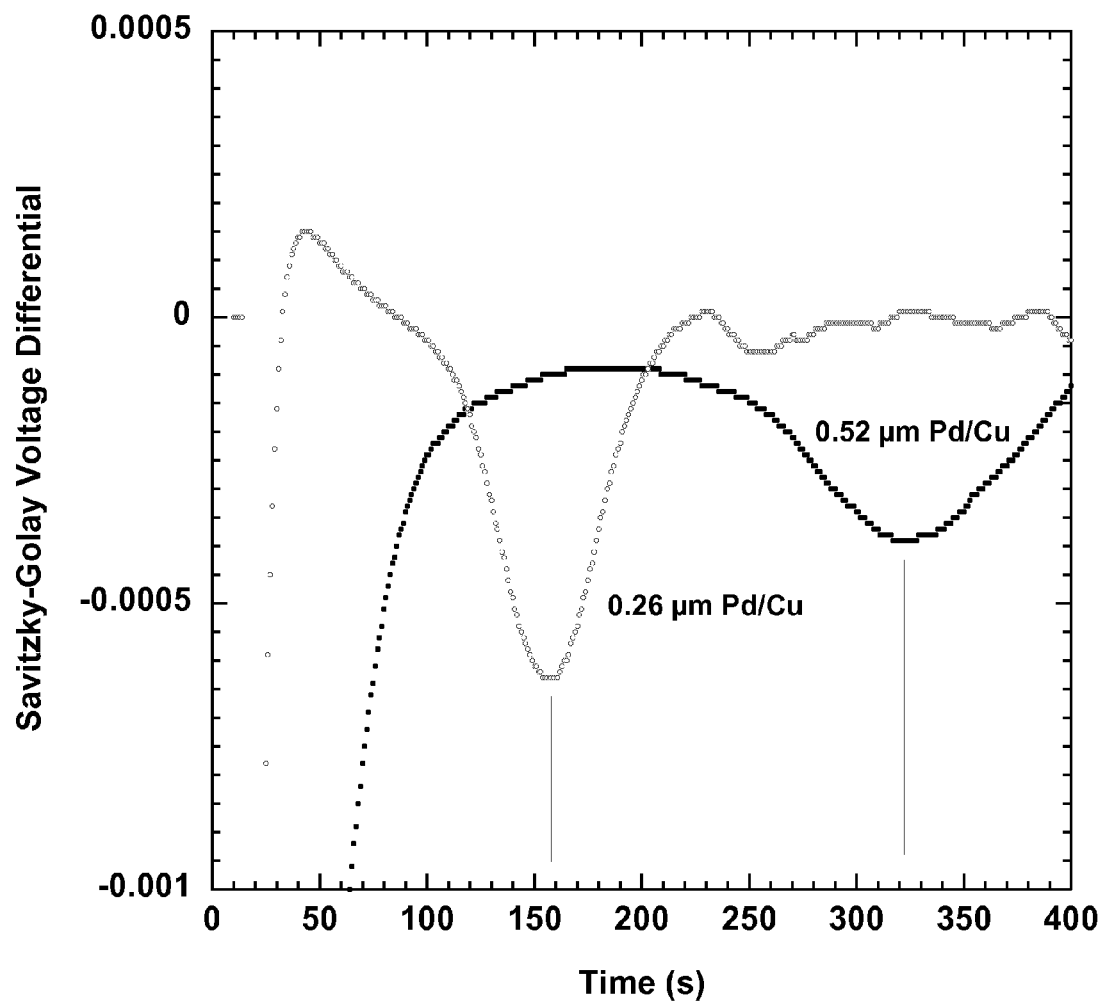
FIG. 12 shows plots of a Savitzky-Golay voltage differential of PATA curves for the third (new) 0.26 μm standard and the second (new) 0.52 μm Pd/Cu standard at −1000 μA/cm$^2$ in the VHC acetate buffer solution (pH 5.0).

For this evaluation, the inflection point in the PATA curve corresponding to the endpoint time was determined by applying Savitzky-Golay data smoothing and first derivative analysis ($2^{nd}$ order polynomial, 15 points to either side of the each data point). As indicated by the Savitzky-Golay voltage differential plots in FIG. 12, this procedure yielded a smooth first-derivative curve with a well-defined minimum corresponding to the endpoint time.

Table 2 summarizes the data obtained for repetitive PATA measurements for the two Pd/Cu standards. For both standards, the average measured thickness was the same as the specified thickness, and the average error was about +/−3 percent. Except for one analysis, the measured thickness was always within +/−8% of the expected thickness.

TABLE 2

PATA Results for 0.26 and 0.52 µm Pd/Cu Standards at −1000 µA/cm² in VHC Acetate Buffer Solution with Savitzky-Golay Endpoint Detection

| Pd Thickness (µm) | Endpoint Time (s) | Measured (µm of Pd) | Error (µm) | Error (%) |
|---|---|---|---|---|
| 0.26 | 158 | 0.25 | −0.01 | −3.8 |
| 0.26 | 166 | 0.26 | 0 | 0 |
| 0.26 | 164 | 0.26 | 0 | 0 |
| 0.26 | 168 | 0.27 | 0.01 | 3.8 |
| 0.26 | 166 | 0.26 | 0 | 0 |
| 0.26 | 148 | 0.23 | −0.03 | −12 |
| 0.26 | 159 | 0.25 | −0.01 | −3.8 |
| 0.26 | 167 | 0.26 | 0 | 0 |
| 0.26 | 175 | 0.28 | 0.02 | 7.7 |
| 0.26 | 169 | 0.27 | 0.01 | 0 |
| Averages | 164 | 0.26 | 0.01 | 3.1 |
| 0.52 | 325 | 0.51 | −0.01 | 1.9 |
| 0.52 | 306 | 0.48 | −0.04 | −7.7 |
| 0.52 | 309 | 0.49 | −0.03 | −5.8 |
| 0.52 | 338 | 0.53 | 0.01 | 2.8 |
| 0.52 | 321 | 0.51 | −0.01 | −1.9 |
| 0.52 | 337 | 0.53 | 0.01 | 1.9 |
| 0.52 | 323 | 0.51 | −0.01 | −1.9 |
| 0.52 | 329 | 0.52 | 0 | 0.0 |
| 0.52 | 339 | 0.54 | 0.02 | 3.8 |
| 0.52 | 338 | 0.53 | 0.01 | 1.9 |
| 0.52 | 353 | 0.56 | 0.04 | 7.7 |
| 0.52 | 336 | 0.53 | 0.01 | 1.9 |
| Averages | 330 | 0.52 | 0.02 | 3.3 |

Wire Specimen Tests

The efficacy of the method and apparatus of the invention for measuring the thickness of Pd coatings on wire specimens was also demonstrated. Chronopotentiometric measurements were performed at −600 µA/cm² on Pd-coated copper wire specimens (20 µm diameter) in a stagnant deaerated pH 5.0 VHC acetate buffer solution (2.0 M sodium acetate+2.0 M acetic acid) using a SurfaceScan® 200 instrument (ECI Technology, Inc.) with a wire attachment fixture. The wire specimen was clamped between two concentric o-rings (2.0 cm inside diameter) so as to define a cylindrical working electrode having a predetermined area (0.013 cm²). The deaerated buffer solution was pumped from a reservoir via a plastic delivery tube, passed through the opening in the concentric o-rings (immersing the predetermined area of the Pd coating), and was returned to the reservoir via a plastic return tube. The reference electrode was in contact with the electrolytic solution in the reservoir and the counter electrode was in contact with the electrolytic solution in the plastic return tube. The coating thickness on the wire specimens was nominally 0.08, 0.10 or 0.12 µm (as specified by wire supplier).

Figure 13:
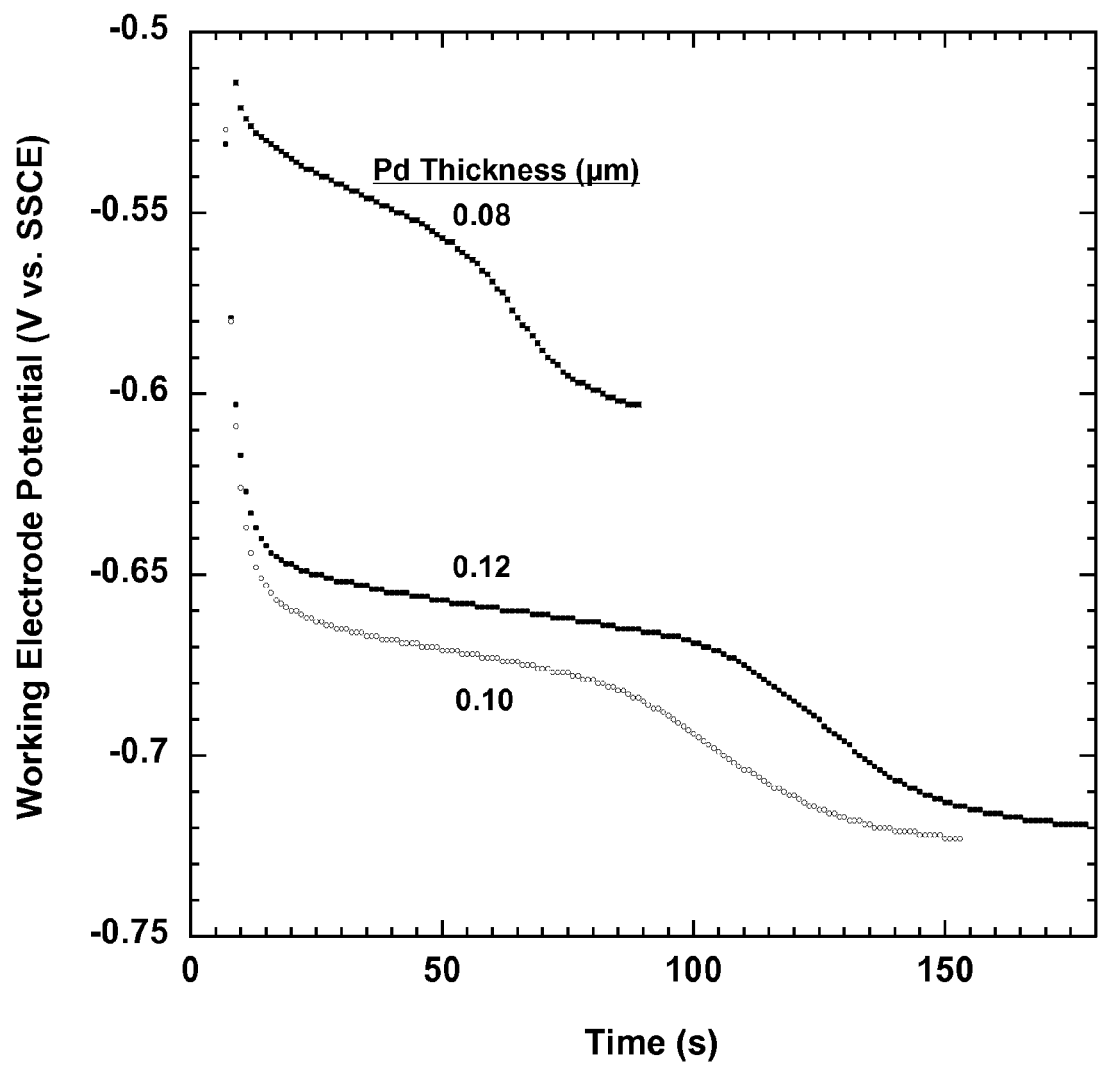
FIG. 13 shows representative PATA curves at −600 μA/cm$^2$ for palladium coatings (0.08, 0.10 and 0.12 μm thick) on copper wire (20 μm diameter) in the VHC acetate buffer (pH 5.0).

FIG. 13 shows representative PATA curves at −600 µA/cm² for palladium coatings (0.08, 0.10 and 0.12 µm thick) on copper wire (20 µm diameter) in the VHC acetate buffer (pH 5.0). These PATA curves are qualitatively and quantitatively very similar to those obtained for flat Pd/Cu specimens. As with the flat specimens, small variations (<30 mV) in the final voltage plateau were observed from specimen to specimen but had little effect on the Pd thickness determination. Likewise, PATA curves for less concentrated acetate buffer solutions (0.5 and 0.1M) exhibited somewhat more variation but yielded comparable average values for the Pd coating thickness.

Table 3 summarizes the PATA results obtained for copper wires (20 µm diameter) with Pd coatings 0.08, 0.10 and 0.12 µm thick. The second derivative of the PATA curves was used to determine the endpoint times. The average Pd thickness measured for the 0.12-µm Pd wire agreed with the specified value (0.12 µm) and the standard deviation was small (6.6%). The average Pd thickness measured for the 0.10-µm Pd wire agreed with the specified value (0.10 µm) and the standard deviation was small (3.3%). Except for one divergent data point (point 2), the Pd thicknesses measured for the 0.0.08-µm Pd wire were highly consistent (standard deviation 3.2%) but the average measured Pd thickness (0.064 µm) was appreciably below the specified Pd thickness (0.080 µm). These results suggest that the thinnest Pd coating had an average thickness (0.064 µm) appreciably less than that specified by the wire supplier (0.08 µm) and was even thinner in some areas. With the divergent data point for the 0.08-µm Pd wire included, the average Pd thickness was 0.062 µm and the standard deviation was still small (8.0%).

TABLE 3

PATA Results for Cu Wires with Pd Coatings of Varied Thickness Measured at −600 µA/cm² in VHC Acetate Buffer Solution

| Measurement Number | Nominal Pd Thickness (µm) | | |
|---|---|---|---|
| | 0.12 | 0.10 | 0.08 |
| 1 | 0.125 | 0.099 | 0.061 |
| 2 | 0.122 | 0.098 | *0.053 |
| 3 | 0.12 | 0.103 | 0.064 |
| 4 | 0.122 | 0.097 | 0.064 |
| 5 | 0.125 | 0.096 | 0.066 |
| 6 | 0.104 | 0.104 | 0.066 |
| Averages | 0.12 | 0.10 | 0.064 |
| Std. Dev. (%) | 6.6 | 3.3 | 3.2 |

*Not included in average and standard deviation

We claim:

1. A method of measuring a thickness of a palladium coating on a substrate, comprising the steps of:
    (1) placing a predetermined area of the palladium coating in contact with an electrolytic solution to form a working electrode;
    (2) placing a counter electrode and a reference electrode in contact with the electrolytic solution;

(3) electrically connecting the working electrode and the counter electrode to an electrical power source, and the working electrode and the reference electrode to an electrical measuring device;

(4) determining the charge density required to electrochemically form a palladium hydride throughout the thickness of the palladium coating; and (5) calculating the thickness of the palladium coating based on the charge density determined in Step (4).

2. The method of claim 1, wherein Step (4) of determining the charge density required to electrochemically form the palladium hydride throughout the thickness of the palladium coating, comprises the steps of:

(a) applying at a cathodic start time a predetermined cathodic perturbation to the working electrode such that a cathodic current flows through the working electrode;

(b) measuring an electrical response of the working electrode to the cathodic perturbation as a function of time;

(c) determining a cathodic endpoint time corresponding to a step in the measured electrical response of the working electrode indicating formation of the palladium hydride throughout the thickness of the palladium coating;

(d) integrating the cathodic current over the time interval between the cathodic start time and the cathodic endpoint time to provide a measured quantity of cathodic charge; and (e) calculating the charge density required to electrochemically form the palladium hydride throughout the thickness of the palladium coating based on the measured quantity of cathodic charge and the predetermined area of the palladium coating.

3. The method of claim 2, wherein the electrical power source is a current source the electrical measuring device is a voltmeter, the predetermined electrical perturbation is a predetermined cathodic current, the measured electrical response is the potential of the working electrode relative to the potential of the reference electrode, and the cathodic endpoint time corresponds to a cathodic step in the potential of the working electrode.

4. The method of claim 3, wherein the predetermined cathodic current may be a constant current of predetermined magnitude or a varied current of predetermined waveform.

5. The method of claim 2, wherein the electrical power source is a voltage source, the electrical measuring device is an ammeter, the predetermined electrical perturbation is a predetermined potential of the working electrode relative to the potential of the reference electrode, the measured electrical response is the cathodic current flowing through the working electrode, and the cathodic endpoint time corresponds to the onset of a substantially flat plateau in the cathodic current.

6. The method of claim 5, wherein the predetermined potential of the working electrode may be a constant potential of predetermined magnitude or a varied potential of predetermined waveform.

7. The method of claim 1, wherein the substrate comprises copper.

8. The method of claim 1, wherein the counter electrode and the reference electrode are the same electrode.

9. The method of claim 1, wherein the palladium hydride substantially comprises the $PdH_{0.58}$ beta-phase.

10. The method of claim 1, wherein the electrolytic solution is a buffer solution having a pH in the 3.0 to 6.0 range.

11. The method of claim 10, wherein the buffer solution is an acetate buffer solution comprising acetic acid and an acetate salt each having a molar concentration in the 0.1 to 10 M range.

12. The method of claim 1, wherein the predetermined area of the palladium coating in contact with the electrolytic solution is defined by a means selected from the group consisting of a gasket, an o-ring, full immersion of the palladium coating in the electrolytic solution, partial immersion of the palladium coating in the electrolytic solution, an adhesive maskant, a curable resin maskant, a gelled electrolytic solution, and combinations thereof.

13. The method of claim 1, further comprising a pretreatment step of:

pretreating the working electrode by applying a predetermined anodic potential or current to the working electrode before the cathodic start time for the palladium thickness measurement such that palladium hydride initially present in the palladium coating of the working electrode is removed by electrochemical oxidation, whereby the quantity of palladium hydride initially present may be measured and the accuracy of the palladium thickness measurement may be improved.

14. The method of claim 1, wherein Step (4) of determining the charge density required to electrochemically form a palladium hydride throughout the thickness of the palladium coating, comprises the steps of:

(a) applying at a cathodic start time a predetermined cathodic perturbation to the working electrode such that a cathodic current flows through the working electrode;

(b) measuring a cathodic response of the working electrode to the cathodic perturbation as a function of time at least until occurrence of a cathodic step in the measured cathodic response of the working electrode indicating formation of the palladium hydride throughout the thickness of the palladium coating of the working electrode;

(c) applying at an anodization start time a predetermined anodic perturbation to the working electrode such that an anodic current flows through the working electrode;

(d) measuring an anodic response of the working electrode to the anodic perturbation as a function of time;

(e) determining an anodic endpoint time corresponding to an anodic step in the measured anodic response of the working electrode indicating substantially complete removal of the palladium hydride within the predetermined working electrode area throughout the thickness of the palladium coating by electrochemical oxidation;

(f) integrating said anodic current over the time interval between the anodization start time and the anodic endpoint time to provide an anodic charge required to electrochemically remove the palladium hydride throughout the thickness of the palladium coating within the predetermined area; and (g) dividing the anodic charge by the predetermined area of the palladium coating to calculate the anodic charge density required to electrochemically remove the palladium hydride throughout the thickness of the palladium coating, said anodic charge density being equivalent in absolute magnitude to the cathodic charge density required to form the palladium hydride throughout the thickness of the palladium coating, wherein the predetermined cathodic perturbation may be a predetermined cathodic current or a predetermined cathodic potential of the working electrode, and the predetermined anodic perturbation may be a predetermined anodic current or a predetermined anodic potential of the working electrode.

15. A method of measuring a thickness of a palladium coating on a substrate, comprising the steps of:
   (1) placing a predetermined area of the palladium coating in contact with an electrolytic solution to form a working electrode;
   (2) placing a counter electrode and a reference electrode in contact with the electrolytic solution;
   (3) electrically connecting the working electrode and the counter electrode to a current source, and the working electrode and the reference electrode to a voltmeter;
   (4) applying at a cathodic start time a predetermined cathodic current to the working electrode by means of the counter electrode and the current source such that a cathodic current flows through the working electrode;
   (5) measuring the potential of the working electrode as a function of time by means of the reference electrode and the voltmeter;
   (6) determining a cathodic endpoint time corresponding to a cathodic step in the measured potential of the working electrode indicating formation of a palladium hydride throughout the thickness of the palladium coating of the working electrode;
   (7) integrating the cathodic current over the time interval between the cathodic start time and the cathodic endpoint time to provide a quantity of cathodic charge passed; and
   (8) calculating the thickness of the palladium coating based on the quantity of cathodic charge passed and the predetermined area of the palladium coating.

16. The method of claim 15, wherein the predetermined cathodic current may be constant or varied with time.

17. The method of claim 15, wherein the palladium hydride is $PdH_{0.58}$, the predetermined current is constant and the thickness of the palladium coating is calculated according to the equation:

$$\text{Pd thickness in } \mu m = \frac{\text{(current density in mA/cm}^2\text{)}\text{(time interval in seconds)}}{632 \text{ mC/cm}^2\text{-}\mu m}.$$

18. The method of claim 15, wherein the measured potential of the working electrode versus time is analyzed graphically to determine the cathodic endpoint time.

19. The method of claim 15, wherein the measured potential of the working electrode versus time is mathematically differentiated to determine the cathodic endpoint time.

20. The method of claim 15, wherein the measured potential of the working electrode versus time is mathematically smoothed and differentiated to determine the cathodic endpoint time.

21. An apparatus for measuring a thickness of a palladium coating on a substrate, comprising:
   (1) a measurement system, comprising
      (a) an electrolytic solution,
      (b) a means of placing a predetermined area of the palladium coating in contact with the electrolytic solution so as to form a working electrode,
      (c) a counter electrode and a reference electrode in contact with the electrolytic solution,
      (d) an electrical power source electrically connected to the working electrode and the counter electrode whereby a predetermined electrical perturbation is applied to the working electrode,
      (e) an electrical measuring device electrically connected to the working electrode and the reference electrode whereby an electrical response to the electrical perturbation applied to the working electrode is measured, and
      (f) a means of determining an endpoint time corresponding to a step in the electrical response of the working electrode;
   (2) a computing device having a memory element with a stored algorithm operative to effect at least Steps (4) and (5) of claim 1; and
   (3) a computer interface enabling the computing device to control the electrochemical analysis system so as to perform said steps of the method of the invention.

22. The apparatus of claim 21, wherein the computing device having a memory element with a stored algorithm is further operative to effect Steps (a)-(e) of claim 2, Steps (a)-(g) of claim 14, or both.

23. The apparatus of claim 21, wherein the reference electrode and the counter electrode are the same electrode.

24. The apparatus of claim 21, wherein the predetermined area of the palladium coating is placed in contact with the electrolytic solution so as to form a working electrode by a means selected from the group consisting of a gasket, an o-ring, full immersion of the palladium coating in the electrolytic solution, partial immersion of the palladium coating in the electrolytic solution, an adhesive maskant, a curable resin maskant, a gelled electrolytic solution, and combinations thereof.

25. The apparatus of claim 21, wherein the means of placing a predetermined area of the palladium coating in contact with the electrolytic solution so as to form a working electrode comprises
   a reservoir containing the electrolytic solution,
   a delivery tube for conveying the electrolytic solution from the reservoir to the predetermined area of the palladium coating,
   a return tube for conveying the electrolytic solution from the predetermined area of the palladium coating back to the reservoir or to a waste container, and
   a liquid pump.

26. The apparatus of claim 21, wherein the memory element is selected from the group consisting of computer hard drive, microprocessor chip, read-only memory (ROM) chip, programmable read-only memory (PROM) chip, magnetic storage device, computer disk (CD), digital video disk (DVD), and combinations thereof.

27. The apparatus of claim 21, wherein the measurement system, the computing device and the computer interface are substantially integrated in a single measurement instrument.

* * * * *